(12) United States Patent
Kim

(10) Patent No.: US 6,855,481 B2
(45) Date of Patent: Feb. 15, 2005

(54) APPARATUS AND A METHOD FOR FORMING A PATTERN USING A CRYSTAL STRUCTURE OF MATERIAL

(76) Inventor: Ki-Bum Kim, Tapmaeul Byuksan APT. 607-1702, Yatap-dong, Puntang-gu, Seongnam-shi, 463-070, Kyonggi-do (KR)

( * ) Notice: Subject to any disclaimer, the term of this patent is extended or adjusted under 35 U.S.C. 154(b) by 169 days.

(21) Appl. No.: 10/220,364

(22) PCT Filed: Jan. 24, 2002

(86) PCT No.: PCT/KR02/00109

§ 371 (c)(1),
(2), (4) Date: Aug. 29, 2002

(87) PCT Pub. No.: WO02/082518

PCT Pub. Date: Oct. 17, 2002

(65) Prior Publication Data

US 2003/0155523 A1 Aug. 21, 2003

(30) Foreign Application Priority Data

Apr. 3, 2001 (KR) .................................... 2001-017694

(51) Int. Cl.[7] .................... G03C 5/00; H01L 29/788; H01L 21/00
(52) U.S. Cl. .................... 430/296; 430/313; 430/942; 250/311; 250/397; 250/398; 250/427; 250/492.3; 257/24; 257/321; 438/22; 438/142; 438/197; 438/478; 438/795

(58) Field of Search ................... 430/296, 313, 430/942; 250/311, 397, 398, 427, 492.3; 257/24, 321; 438/22, 142, 197, 478, 795

(56) References Cited

U.S. PATENT DOCUMENTS

| 5,229,320 A | * | 7/1993 | Ugajin ..................... 438/694 |
| 6,194,237 B1 | * | 2/2001 | Kim et al. ................. 438/22 |
| 6,376,839 B1 | * | 4/2002 | Hayles et al. ............. 250/311 |
| 6,424,004 B2 | * | 7/2002 | Kim et al. ................. 257/321 |

FOREIGN PATENT DOCUMENTS

| JP | 08274298 A | 10/1996 |
| JP | 11111618 A | 4/1999 |
| JP | 2000173446 | 6/2000 |

* cited by examiner

*Primary Examiner*—Christopher G. Young
(74) *Attorney, Agent, or Firm*—Grossman, Tucker, Perreault & Pfleger, PLLC

(57) ABSTRACT

The present invention relates generally to an apparatus and a method for forming a pattern, and in particular, to an apparatus and a method for forming a pattern for the formation of quantum dots or wires with 1~50 nm dimension using the atomic array of a crystalline material and to the manufacture of functional devices that have such a structure.

In the present invention, the functional device means an electronic, magnetic, or optical device that can be fabricated by procedures including the formation process of quantum dots or wires.

20 Claims, 24 Drawing Sheets

| CRYSTAL SYSTEMS | P | C | I | F |
|---|---|---|---|---|
| TRICLINIC |  | | | |
| MONOCLINIC |  |  | | |
| ORTHORHOMBIC |  |  |  |  |
| TETRAGONAL |  | |  | |
| RHOMBOHEDRAL |  | | | |
| HEXAGONAL |  | | | |
| CUBIC |  | |  |  |

0.543nm 0.543nm 0.565nm

APPARATUS AND A METHOD FOR FORMING A PATTERN USING A CRYSTAL STRUCTURE OF MATERIAL

BACKGROUND OF THE INVENTION

1. Field of the Invention

The present invention relates generally to an apparatus and a method for forming a pattern, and in particular, to an apparatus and a method for forming a pattern for the formation of quantum dots or wires with 1~50 nm dimension using the atomic array of a crystalline material and to the manufacture of functional devices that have such a structure.

In the present invention, the functional device means an electronic, magnetic, or optical device that can be fabricated by procedures including the formation process of quantum dots or wires.

2. Description of the Related Art

The formation process of quantum dots or wires becomes the core process for the fabrication of an electronic, magnetic or optical device with quantum dots or wires as the application of such devices is increasingly expected. A fundamental operating principle of such devices is based on quantum mechanical results that the physical properties of the particle are greatly affected by its size as it becomes nanometer-sized. Particularly, there are many researches for the single electron transistor which has been suggested as the alternative to MOS device in order to overcome the limitation of the MOS device that has been developed continuously for 40 years.

Previous researches on the formation processes of quantum dots or wires can largely be divided as follows.

First, there is a method in which one or a few quantum dots or wires are formed by AFM (Atomic Force Microscopy), STM (Scanning Tunneling Microscopy) and electron beam lithography. This method has the capability to form the quantum dots or wires whose size and location are controlled experimentally, but has difficulty in applying to mass production because of a low throughput.

Second, there is a method in which quantum dots or wires are formed by the process of patterning and etching. In this method, patterning means the formation process of quantum dots or wires on the substrate by the electron beam direct-writing, or by the etching of the chemical substance which was imprinted by the mask or mold made with an electron beam.

Third, there is a method in which quantum dots or wires are formed by the nucleation at the early state of phase transition of materials. This method has can be applied to mass production, but has problems in controlling the size, density or distribution of quantum dots or wires.

SUMMARY OF THE INVENTION

Therefore, it is an object of the present invention to provide an apparatus and a method for forming a pattern using a crystal structure of a material as a mask.

It is another object of the present invention to provide an apparatus and a method for forming quantum dots and wires of uniform size and density which can be controlled by patterning a layer using a crystal structure of a material as a mask.

It is a further object of the present invention to provide an apparatus and a method for forming quantum dots and wires using a crystal structure of a material for fabricating semiconductor devices in practice.

It is still another object of the present invention to provide a semiconductor device having the structure of quantum dots or wires.

The foregoing and other objects of the present invention can be achieved by providing an apparatus and a method for forming a pattern using a crystal structure of a material as a mask.

According to one aspect of the present invention, an apparatus for forming a pattern using a crystal structure of a material which is modified from a Transmission Electron Microscopy (TEM) is comprising an electron gun for radiating electrons to pass through said material; a first means for focusing said electrons radiated by said electron gun; a second means for focusing said electrons on a uniform spot; a loading means for loading said material which is passed through by said electrons; a forming means for forming a lattice image using a diffracted beam and a transmitted beam split during passing through said material; a plurality of lenses for scaling up or down said lattice image formed by said forming means; and an irradiated material mover for inserting said irradiated material between said plurality of lenses for making the formation of said lattice image of predetermined size.

Preferably, said material having a crystal structure is processed into a thickness of a few tens of nanometer.

Preferably, said irradiated material is a semiconductor substrate.

Preferably, said irradiated material mover is a wafer-mover comprising a wafer cassette installed a plurality of wafers and inserts said wafer between said plurality of lenses.

Preferably, said semiconductor substrate has been applied with photo-resist film after deposition of gate oxide and amorphous silicon on the substrate in which source and drain regions are already formed.

According to another aspect of the present invention, a method for forming a pattern using a crystal structure of a material is comprising the steps of locating said material having a crystal structure in the chamber of the transmission electron microscopy; radiating an electron beam to said material; forming a pattern from a lattice image of said material formed as a result of interference between a diffracted electron beam and a transmitted electron beam passed through said material on the surface of an irradiated material.

Preferably, said lattice image is formed by a method of the phase contrast imaging.

Preferably, said material having crystal structure is processed into a thickness of a few tens of nanometer.

Preferably, said irradiated material is a photoresist material on a semiconductor substrate.

Preferably, said semiconductor substrate has been applied with photo-resist material after deposition of a gate oxide and an amorphous silicon on the substrate in which source and drain regions are already formed.

BRIEF DESCRIPTION OF THE DRAWINGS

The above and other objects, features and advantages of the present invention will become more apparent from the following detailed description when taken in conjunction with the accompanying drawings in which:

FIG. 5C is rotated 56° clockwise and 15° azimuthally.

FIG. 6C is rotated 56° clockwise and 15° azimuthally.

DETAILED DESCRIPTION OF THE PREFERRED EMBODIMENTS

Hereinafter, preferred embodiments of the present invention will be described in detail with reference to the accompanying drawings. In the following description, well-known functions or constructions are not described in detail.

At first, to help understanding of the invention, crystal structures of general materials and their various schematic figures will be illustrated.

It is well known that the materials in the earth are composed of atoms and molecules which contain a few atoms and particularly, solid material is classified into a crystalline material in which the atoms are situated in a repeating or periodic array over large atomic distances and an amorphous material which lacks a systematic and regular arrangement of atoms over relatively large atomic distances. The research on the periodic array of the atoms started in 1912 by Max von Laue who found x-ray diffraction. In 1913 W. H. Bragg and his son solved the crystal structure of diamond and salt by x-rays and in 1920 Ewald introduced the concept of the reciprocal lattice. Until now, the crystal structures of more than a hundred thousand of organic or inorganic compounds in the earth have discovered.

Figure 1A:
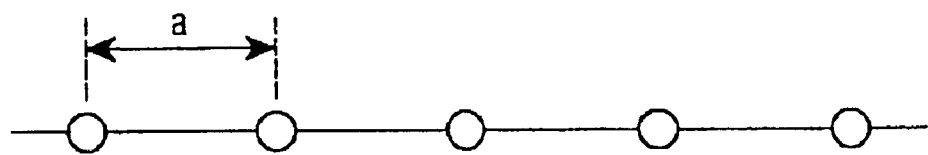
FIGS. 1A to 1C illustrate lattice points moved one-dimensional, two-dimensional, three-dimensional respectively.

If a point is moved by the distance a parallel to a certain direction, it matches second point and if that is moved the same way, that becomes third point. As the same way one point is moved parallel repeatedly, an array of points is made as shown FIG. 1A. This array of points which is generated with being repeatedly shifted at regular distance along the given direction is called lattice. The motion of shifting a point in this manner is called translation and expressed as vector a. Here regular distance, that is, the magnitude of the vector |a|=a is called period or unit period. In this array of points, each point is the same and if one point is marked as an origin.

That is, r=ma where m is an integer from $-\infty$ to $-\infty$.

Figure 1B:
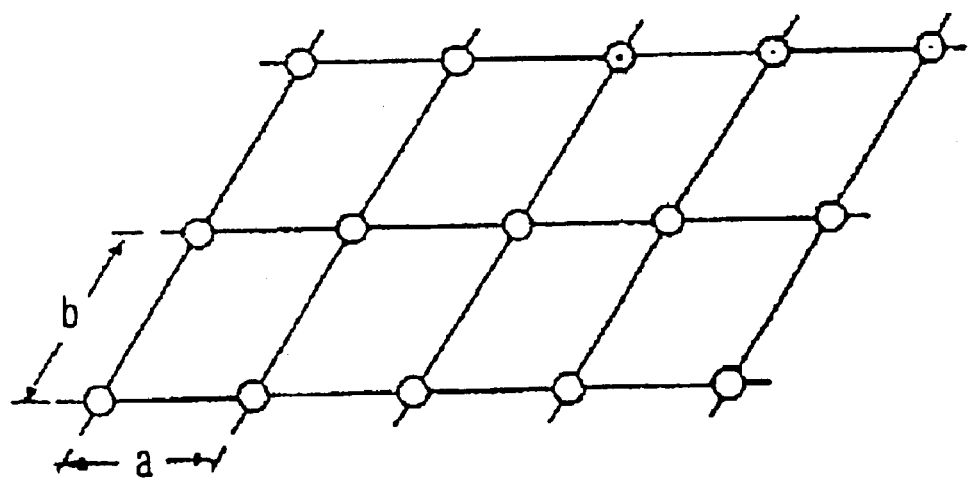
Figure 1C:
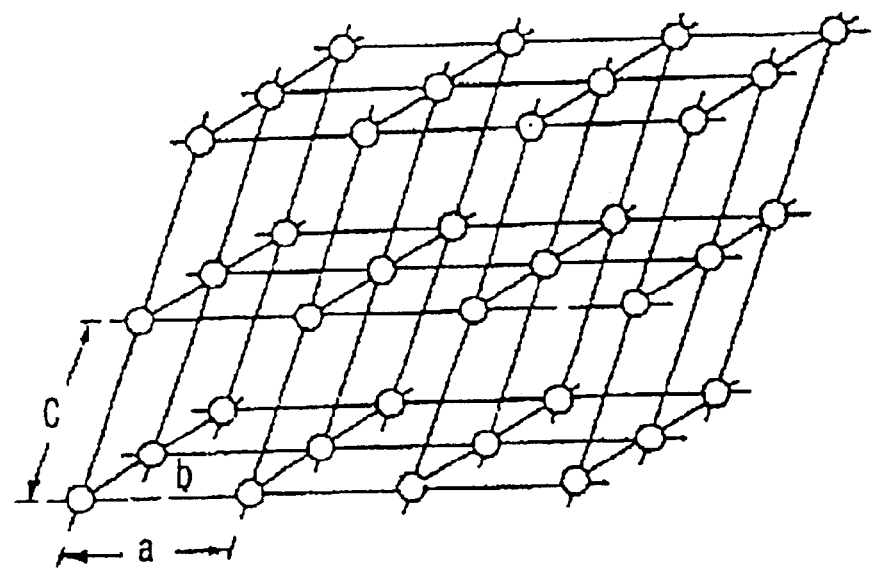

Point network plane is generated by translation this array of points to the other direction as shown FIG. 1B and this is called lattice plane. When this lattice plane is translated to translation c, the third direction which is not parallel to this plane, three dimensional point network plane is generated and called space lattice. In this space lattice, each lattice point is described by position vector r from the origin and expressed as, r=ma+nb+pc
where, m, n, p are integers between $-\infty$ to $\infty$. The space lattice is infinitely spread in infinite space as shown FIG. 1C.

Figure 2:
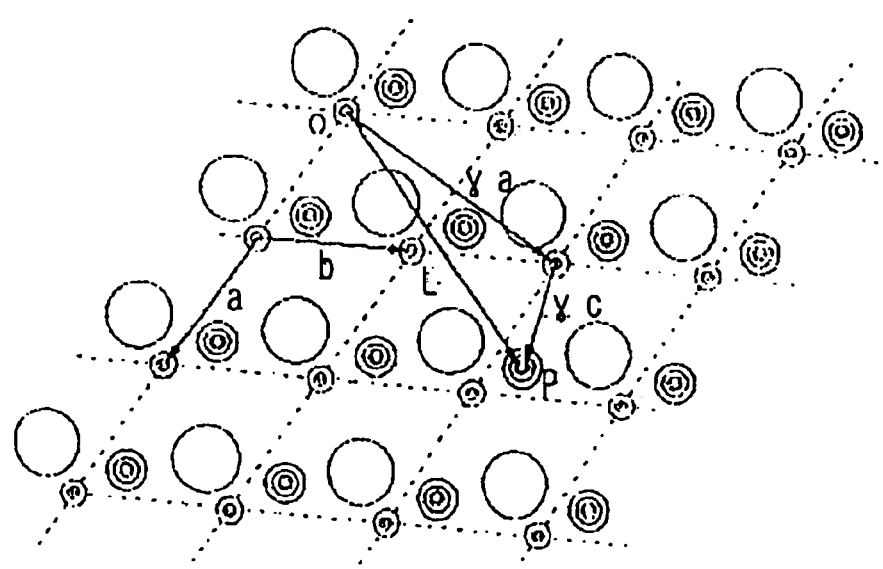
FIG. 2 illustrates an arrangement of atoms around the lattice point.

It is said that a crystal is macroscopically uniform, because the properties of a part of crystal are the same as those of the other part at arbitrary distance away. FIG. 2 shows an imaginary crystal structure. A certain point p in this crystal is described by the position vector, L, and the unit translation vectors of this lattice a, b, c, $$L = Xa + Yb + Zc$$
$$= (m+x)a + (n+y)b + (p+z)c$$
$$= (ma+nb+pc) + (xa+yb+zc)$$
$$= r + rl$$

where, X, Y, Z are real numbers and x, y, z are decimals between 0 and 1. That is, a certain point in space is expressed by rl which represents a crystal lattice, and r which represents position vector in the lattice. Here, the unit lattice described by three translation vectors is called a unit cell.

When a certain point in the crystal is fixed as the origin (0,0,0), all lattice points generated from this point (0,0,0) are identical with the origin and have the same properties. That is to say, whatever point is fixed as the origin in the crystal, every lattice point made by translation from this point is identical. Identical means all properties (including the geometric form of the surroundings around this point, chemical properties such as a kind of neighbor atoms, or physical properties such as electron density, potential difference) are exactly the same.

All crystalline includes one of the 7 crystal systems by the relation between three vectors, a, b, c that determine unit cell. TABLE 1 shows the relation between lattice parameters which defines three axes of unit cell.

TABLE 1

| Crystal structure | Crystal system | Lattice parameter |
|---|---|---|
| Cubic | Cubic | A = b = c |
|  |  | α = β = γ = 90° |
| Hexagonal | Hexagonal | A = b ≠ c |
|  |  | α = β = 90°  γ = 120° |
| Trigonal | Rhombohedral | A = b = c |
|  |  | α = β = γ ≠ 90° |
| Tetragonal | Tetragonal | A = b ≠ c |
|  |  | α = β = γ = 90° |
| Orthorhombic | Orthorhombic | A = b = c |
|  |  | α = β = γ = 90° ≠ |

TABLE 1-continued

| Crystal structure | Crystal system | Lattice parameter |
|---|---|---|
| Monoclinic | Monoclinic | 1. c-unique $a \neq b \neq c$ $\alpha = \beta = 90° \neq \gamma$ |
| Monoclinic | Monoclinic | 2. b-unique $a \neq b \neq c$ $\alpha = \gamma = 90° \neq \beta$ |
| Triclinic | Triclinic | $A \neq b \neq c$ $\alpha \neq \beta \neq \gamma \neq 90°$ |

Figure 3:
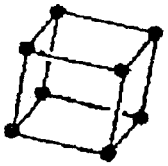
FIG. 3 illustrates the 7 crystal systems and the 14 Bravais lattices.
Figure 3:
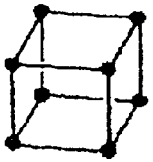
Figure 3:
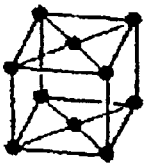
Figure 3:
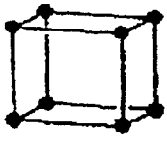
Figure 3:
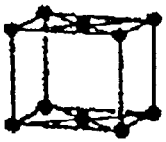
Figure 3:
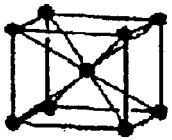
Figure 3:
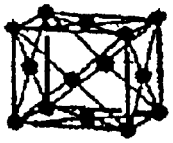
Figure 3:
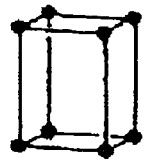
Figure 3:
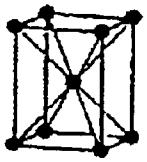
Figure 3:
Figure 3:
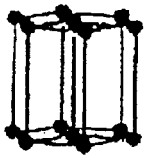
Figure 3:
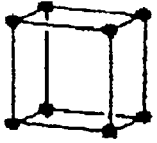
Figure 3:
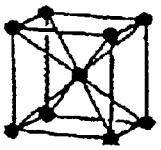
Figure 3:

Also all crystalline have one of the 14 Bravais lattices as shown in FIG. 3. It is classified according to the number of lattice points in unit cell as the primitive cell (P) has one lattice point in unit cell, the base-centered cell (A, B or C) has one lattice point in the center of one plane, the face-centered cell (F) has lattice points in the center of each plane and the body-centered cell (I) has one lattice point in the center of the unit cell.

The crystal structure, of which more than a hundred thousand of organic or inorganic materials have been known until now, is classified as the 7 crystal systems and the 14 Bravais lattices. Actual crystal structure is composed by the arrangement of one or more of the same or different atoms in each lattice point which is included in the 14 Bravais lattice.

Next, some examples of such a crystal structure are given and the pattern from the arrangement of atoms which is shown when those crystal structures are projected to the given crystallographic orientation is explained.

Figure 4A:
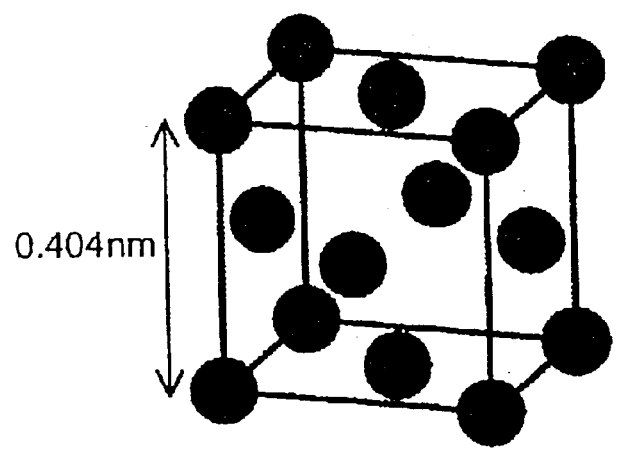
FIG. 4A illustrates a unit cell of crystal structure of Al.
Figure 4B:
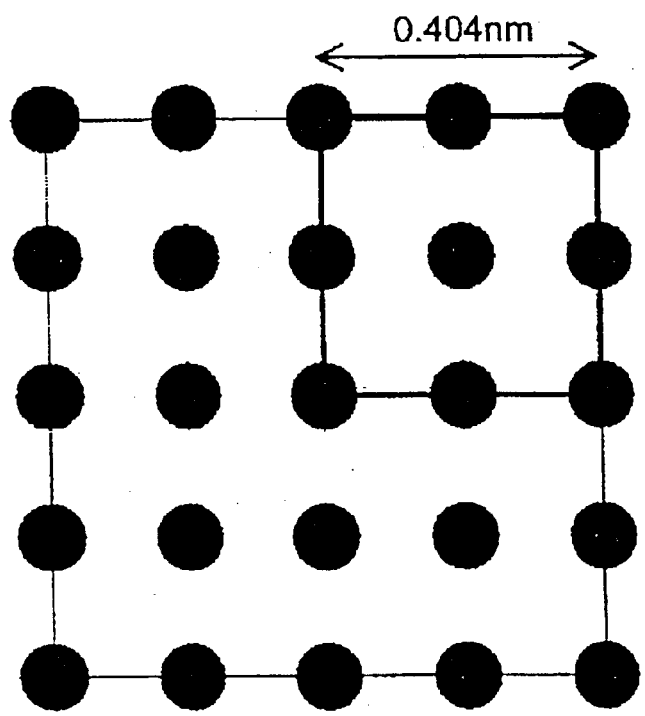
FIGS. 4B to 4D illustrate two-dimensional projection patterns of Al crystal through the [100], [110], [111] crystallographic orientations respectively.
Figure 4C:
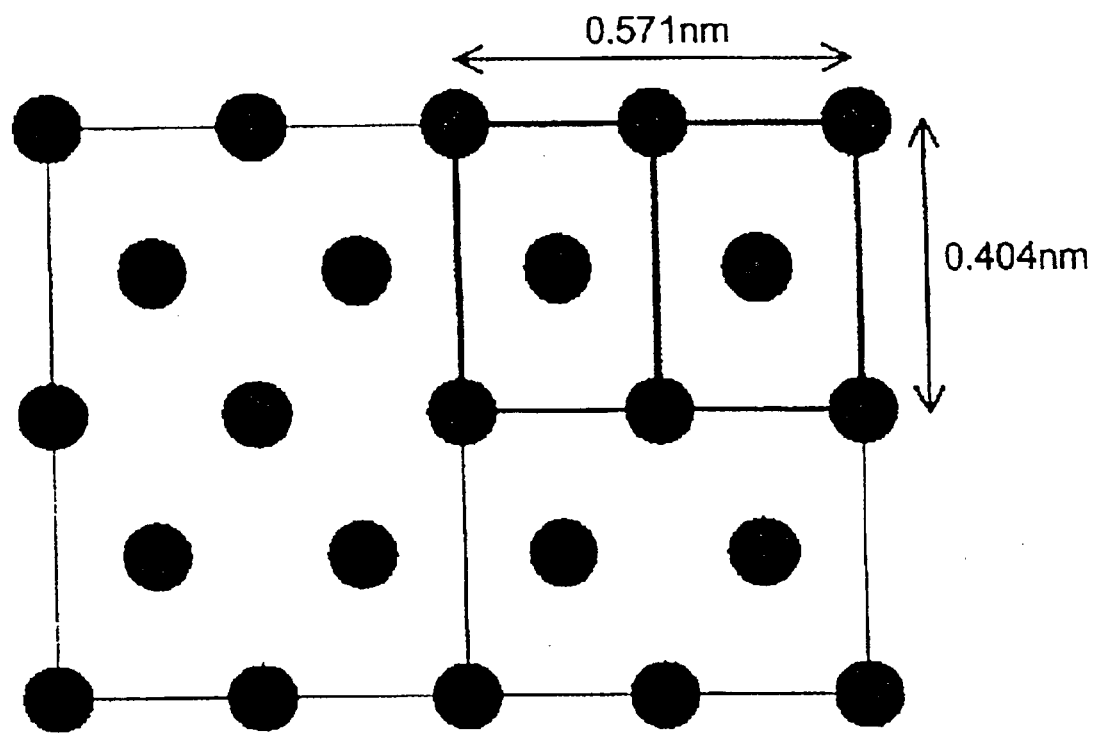
Figure 4D:
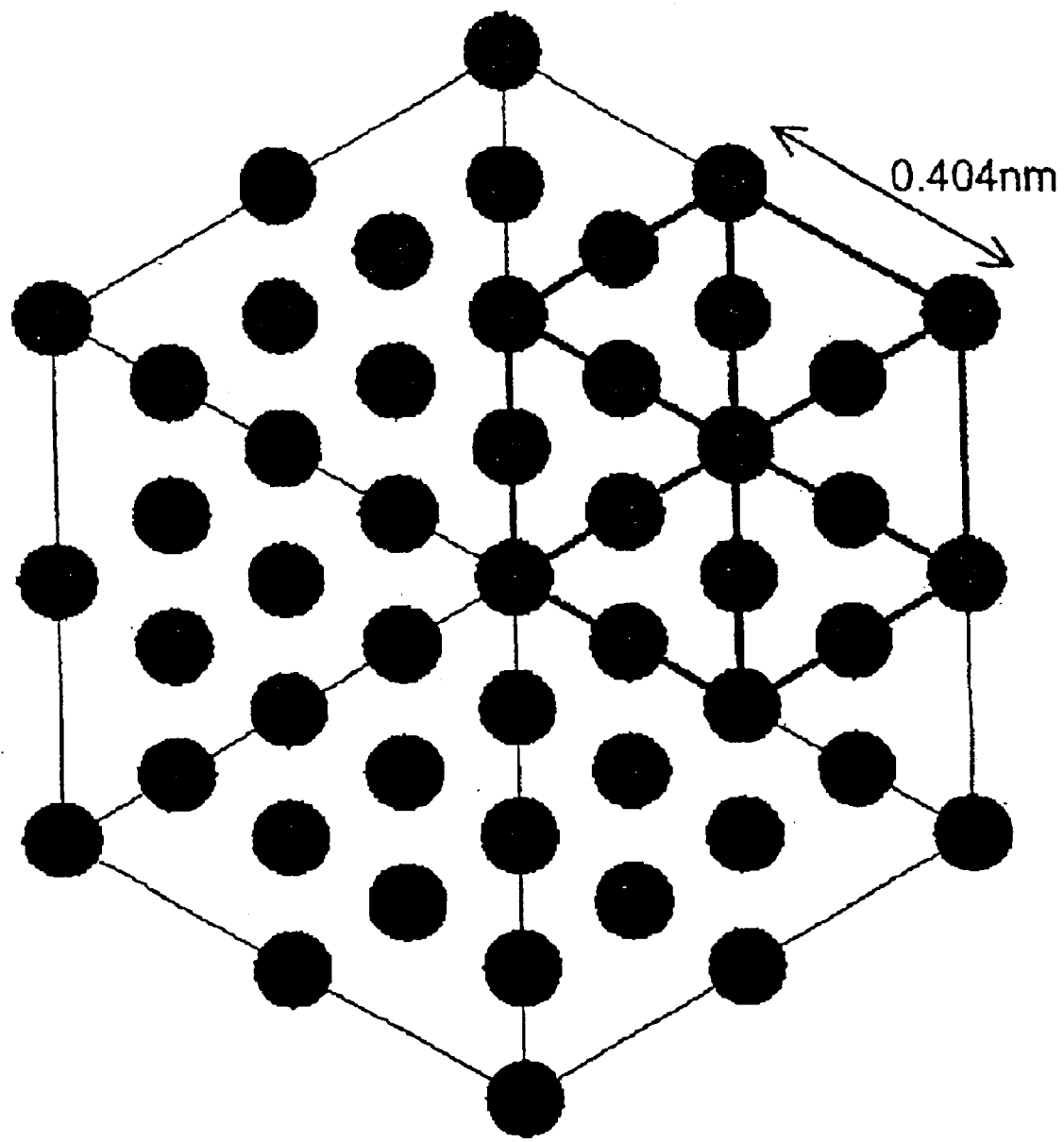

For example, Al is a cubic crystal system (a=b=c) and the face-centered cell of the Bravais lattices, so it has four lattice points in one unit cell. The crystal structure of Al is made when one Al atom lies in one lattice point, and the lattice constant of Al is a=b=c=0.404 nm. Therefore the structure of Al unit cell is shown as FIG. 4A. FIGS. 4B, 4C, and 4D show the projection pattern of atomic arrangement through [100], [110] and [111] crystallographic orientations.

Figure 5A:
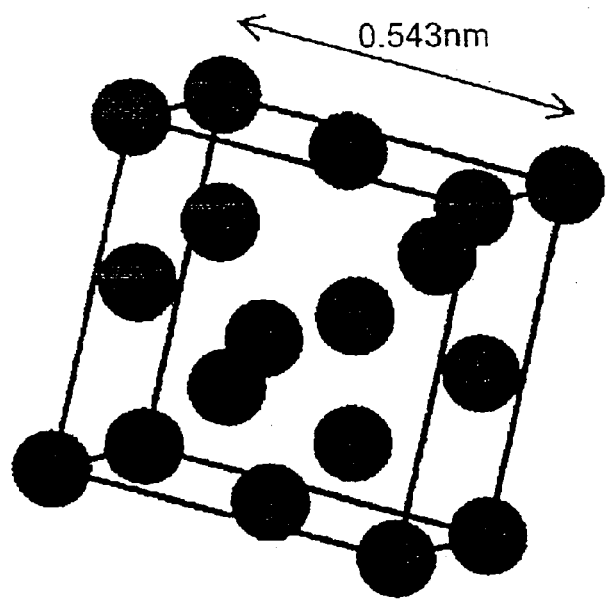
FIG. 5A illustrates a unit cell of crystal structure of Si.
Figure 5B:
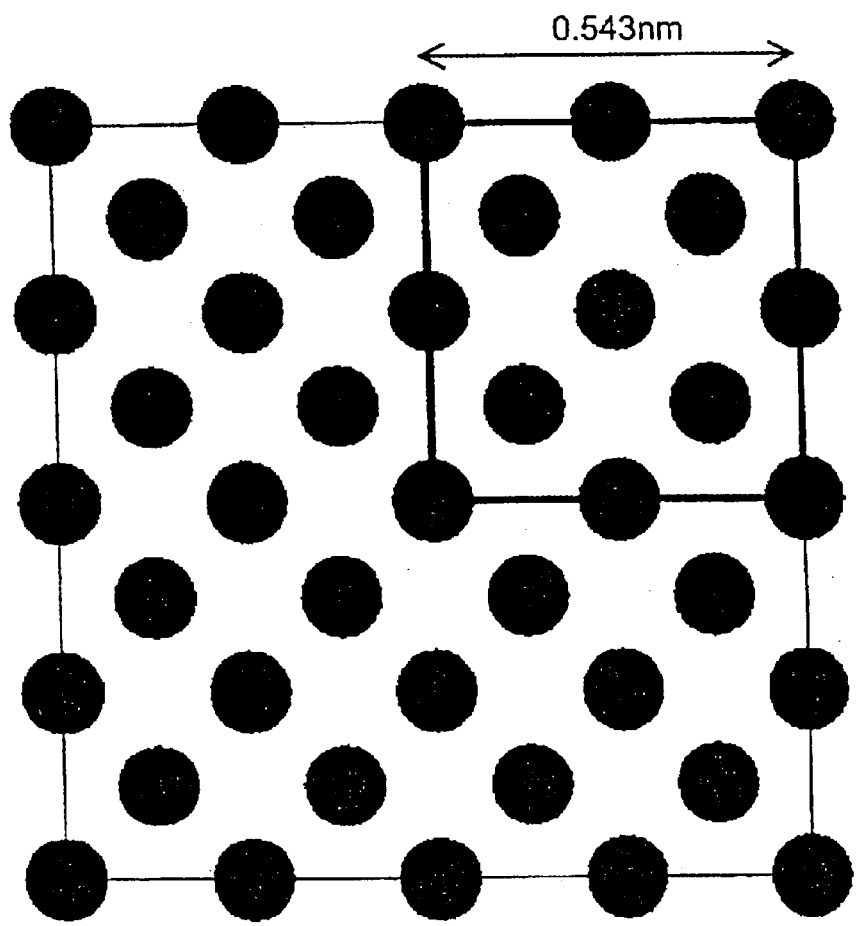
FIGS. 5B to 5D illustrate two-dimensional projection patterns of Si crystal through the [100], [110], [111] crystallographic orientations.
Figure 5C:
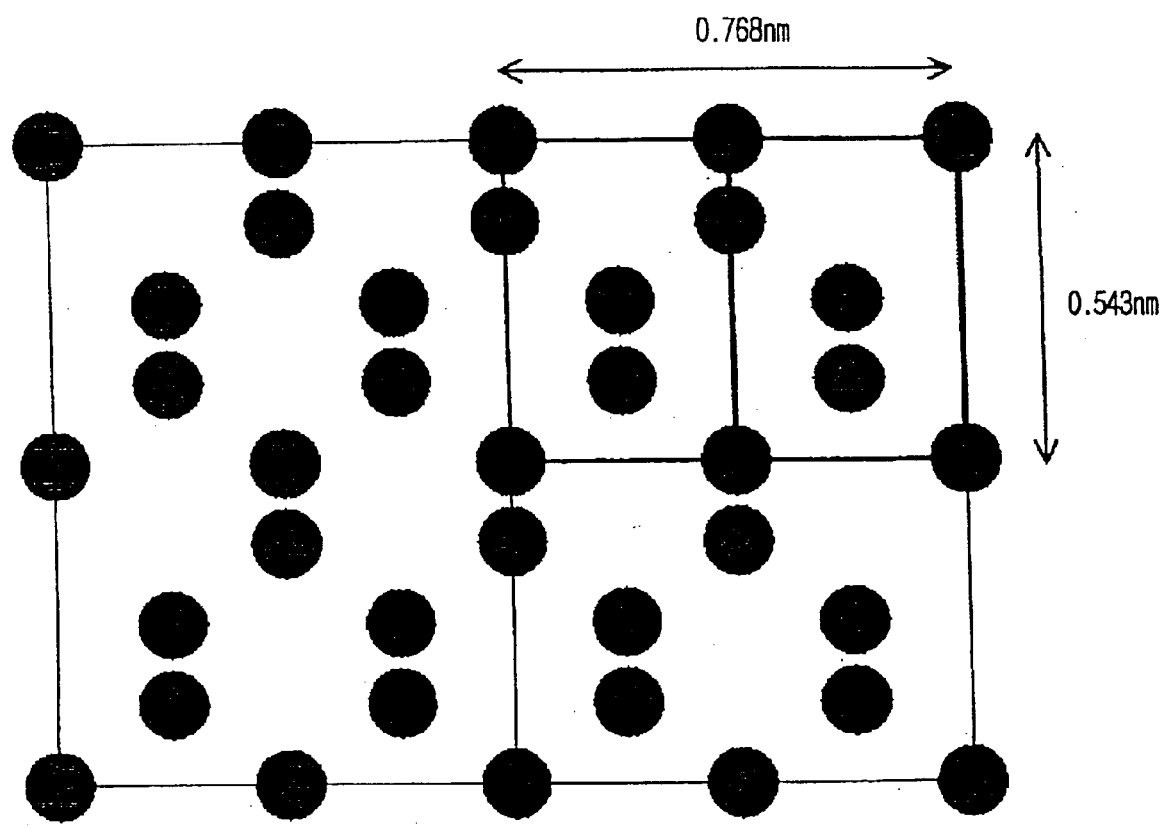
Figure 5D:
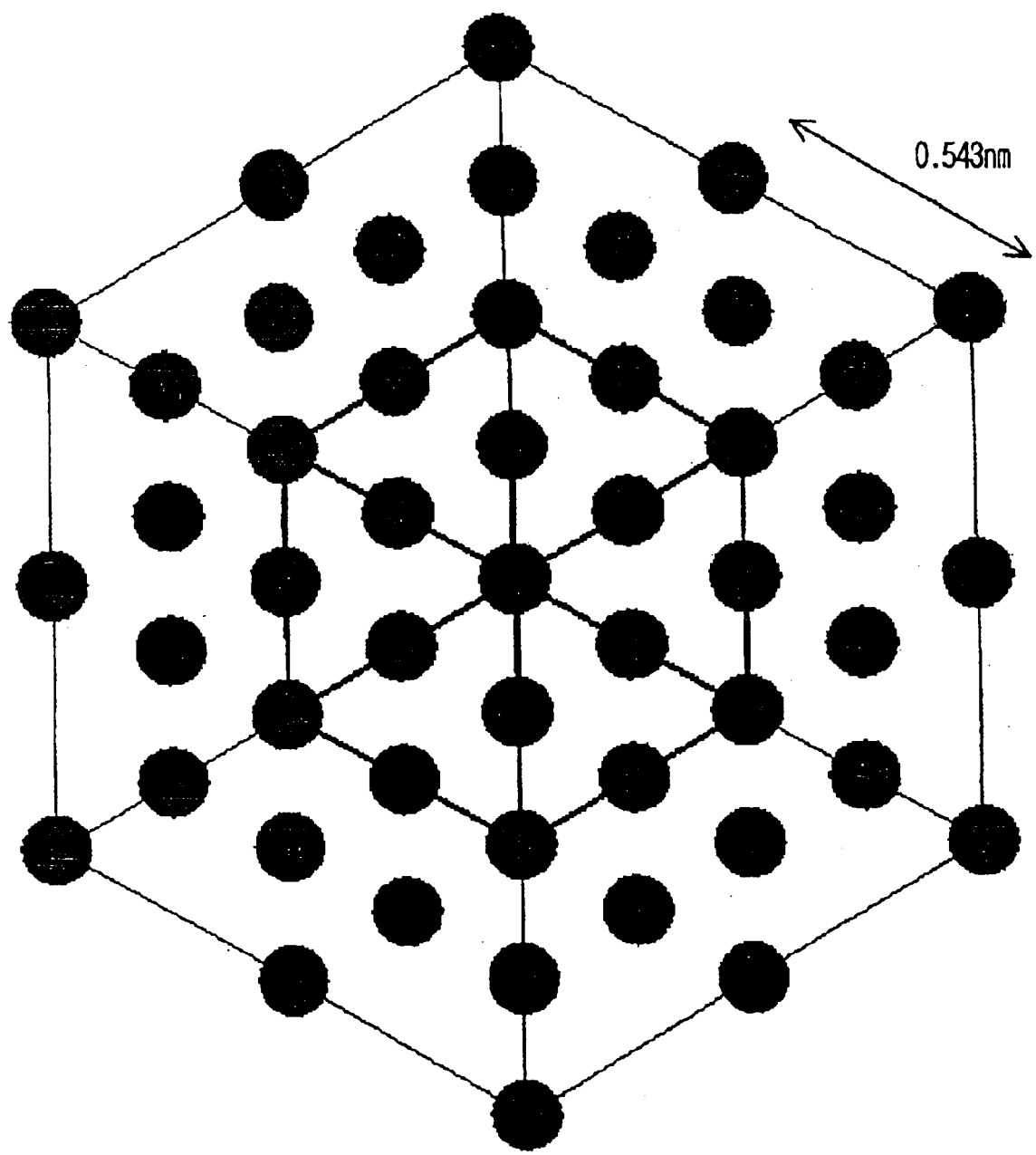
Figure 5E:
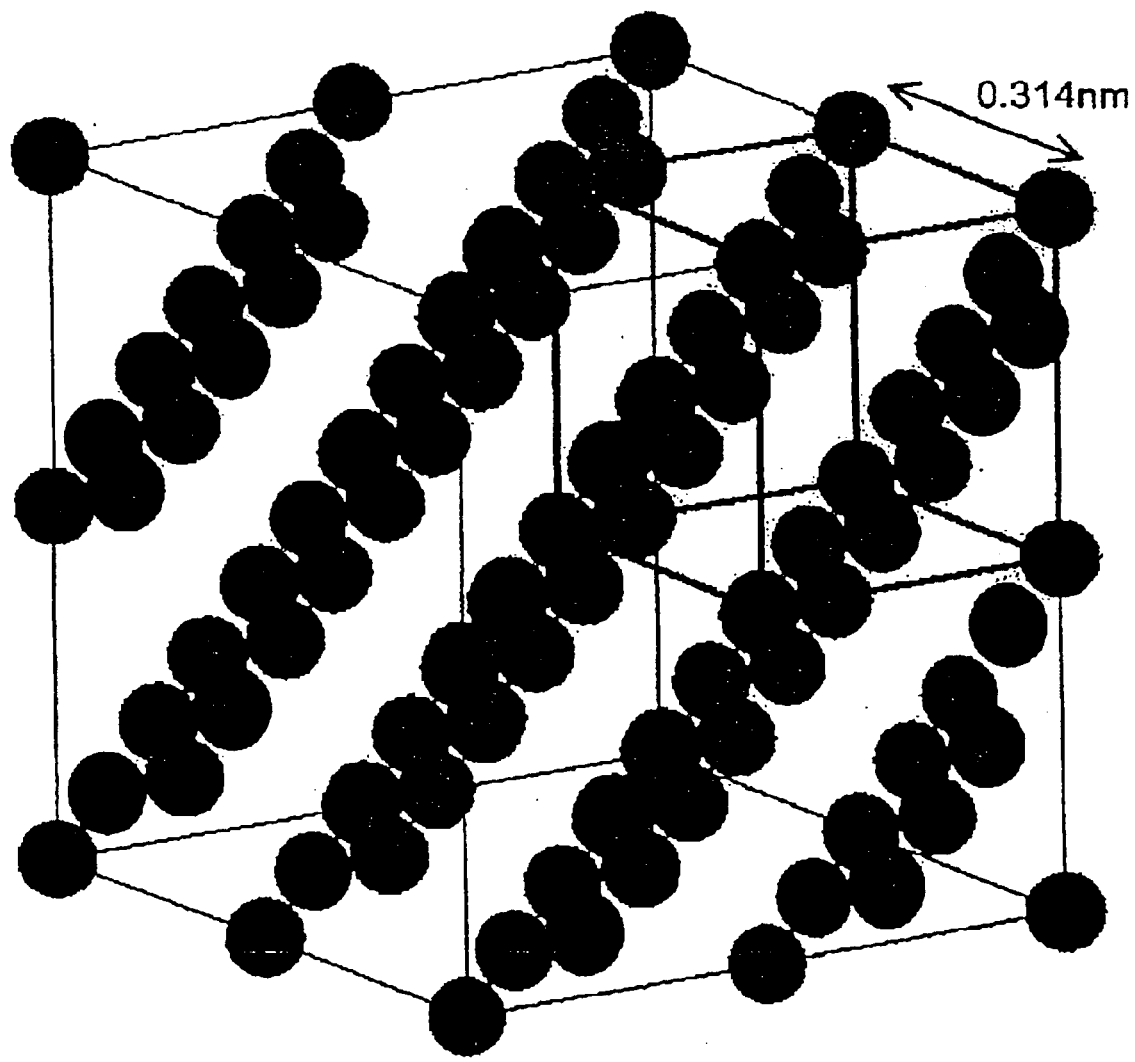
FIG. 5E illustrates a three-dimensional projection pattern when

The other example is Si of a diamond crystal structure. Si is cubic crystal system and the face-centered of the Bravais lattices like Al (Face Centered Cubic). So it has four lattice points in one unit cell, but it has two atoms in one lattice point unlike simple face-centered cubic crystal system (lattice parameter a=b=c=0.543 nm). Therefore there are eight atoms in a Si unit cell. FIG. 5A shows the unit cell of Si. As the same way FIGS. 5B, 5C and 5D show the two-dimensional projection pattern of atomic arrangement through [100], [110] and [111] crystallographic orientations. FIG. 5E shows the pattern when FIG. 5B is rotated 56° clockwise and 15° azimuthally. As shown FIG. 5C, the image looks like several lines. This is the evidence that depending on processing techniques, Si single crystal can apply to the form of quantum wires in a single electron transistor device.

Figure 6A:
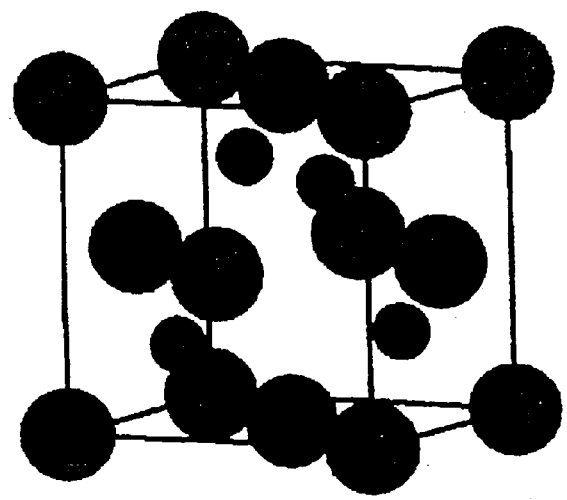
FIG. 6A illustrates a unit cell of crystal structure of GaAs.
Figure 6B:
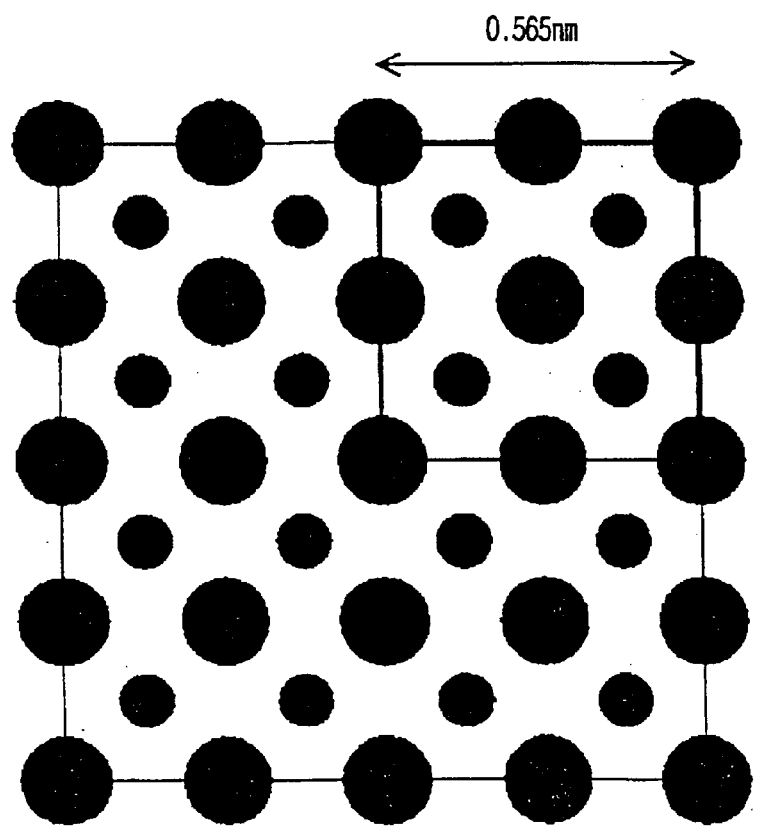
FIGS. 6B to 6D illustrate two-dimensional projection patterns of GaAs crystal through the [100], [110], [111] crystallographic orientations.
Figure 6C:
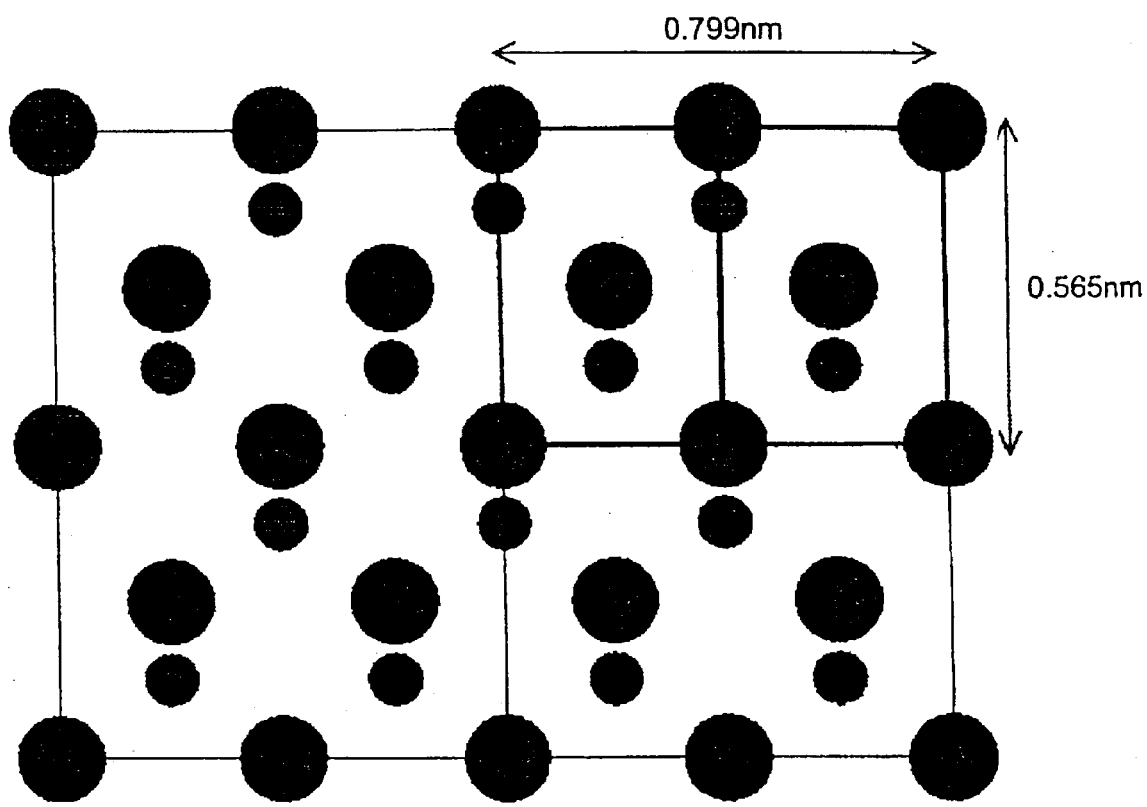
Figure 6D:
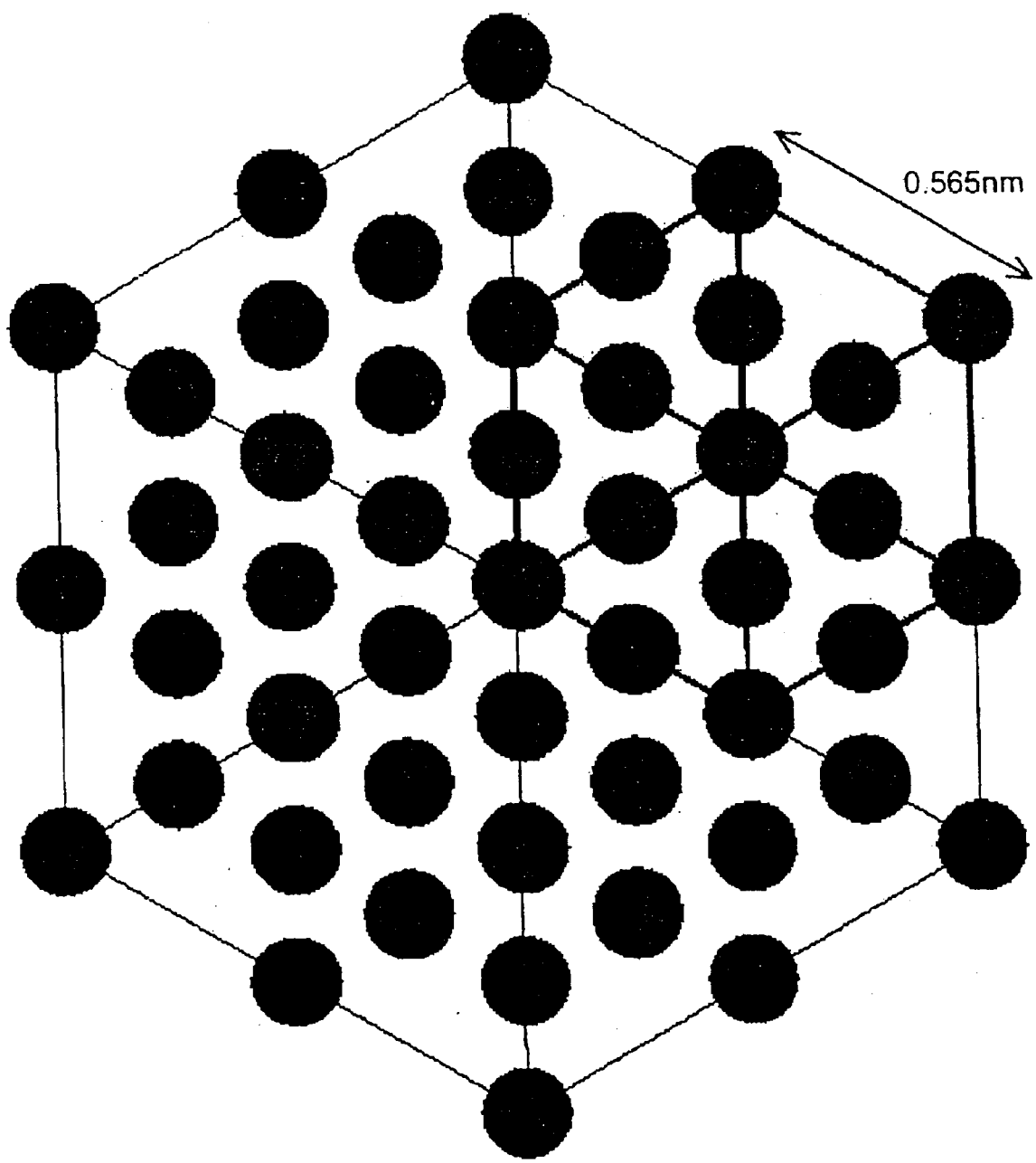
Figure 6E:
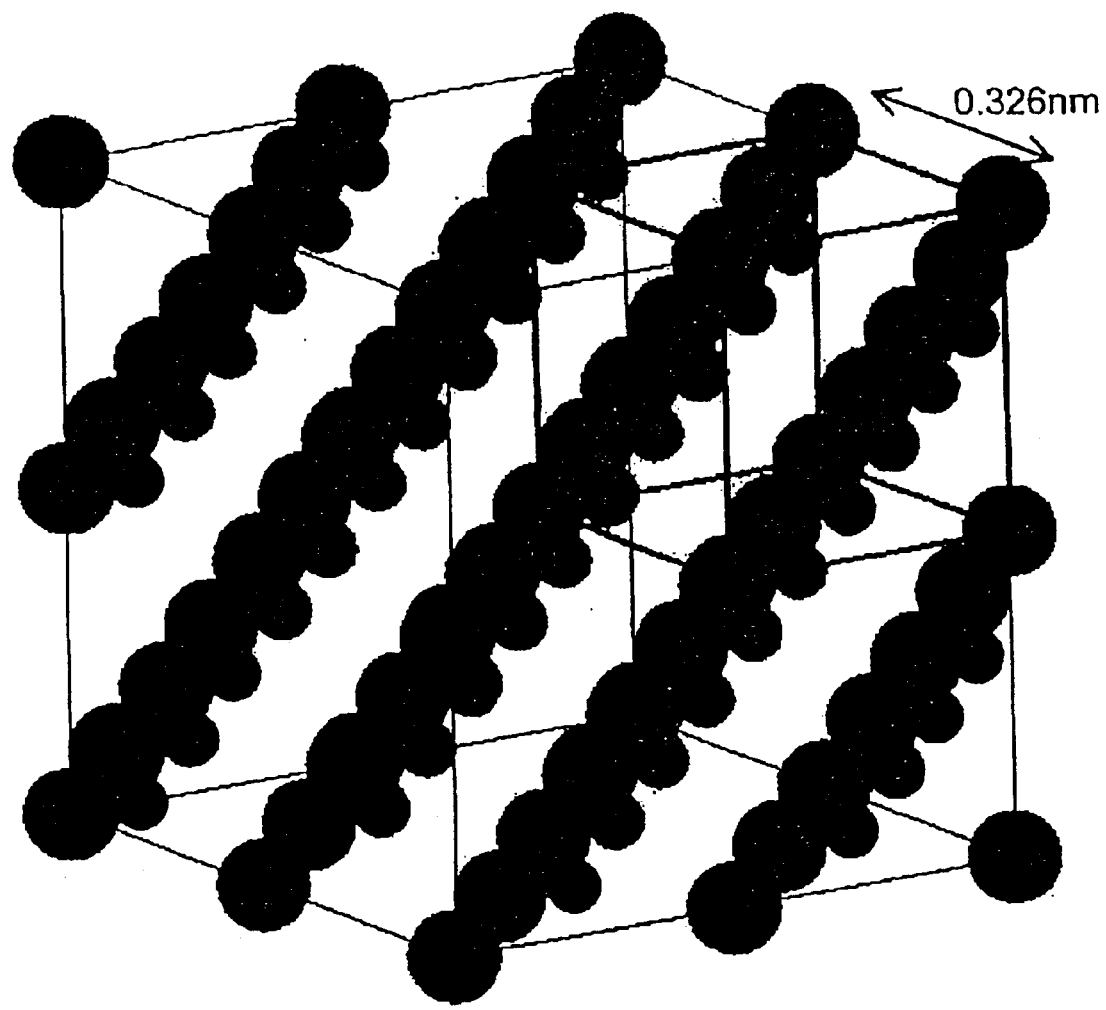
FIG. 6E illustrates a three-dimensional projection pattern when

And another example is the crystal structure of GaAs. GaAs has a crystal structure of cubic like Al and Si, and the face-centered Bravais lattice like Si. But, unlike Al of a simple cubic lattice and Si of a diamond crystal structure, GaAs has a crystal structure which is an one Ga atom and one As atom at one lattice point.(lattice parameter a=b=c= 0.565 nm) FIG. 6A shows the unit cell of crystal structure of GaAs. By the same way, FIGS. 6B, 6C, 6D are two-dimensional projection patterns of GaAs crystal through the [100], [110], [111] crystallographic orientations. FIG. 6E shows the pattern when FIG. 6C is rotated 56° clockwise and 15° azimuthally in the same manner of FIG. 5E. Like Si, the single crystal of GaAs is a good example applicable to the quantum wire formation.

Al, Si, and GaAs mentioned above are only a few examples among the already known crystal structures over a hundred thousand. Thus, these demonstrations indicate that very various patterns generated by electrons transmitted in the two dimensional plane can be obtained. Of course, this generated pattern is dependent on the crystallographic orientation as well as on the crystal structure.

The atom's array of the crystal can be observed using the phase-contrast method in high resolution TEM (transmission electron microscopy). As the electron microscopy has developed, it is possible to distinguish the atoms alignments with the range of 0.14 nm–0.20 nm under 200 kV-300 kV of an accelerating voltage.

In the phase contrast method, atomic images can be made by the phase difference between diffracted electron beam and transmitted electron beam which is generated from the crystal material. This method has a much better resolution than other methods such as a diffraction contrast or an absorption contrast.

Figure 7:
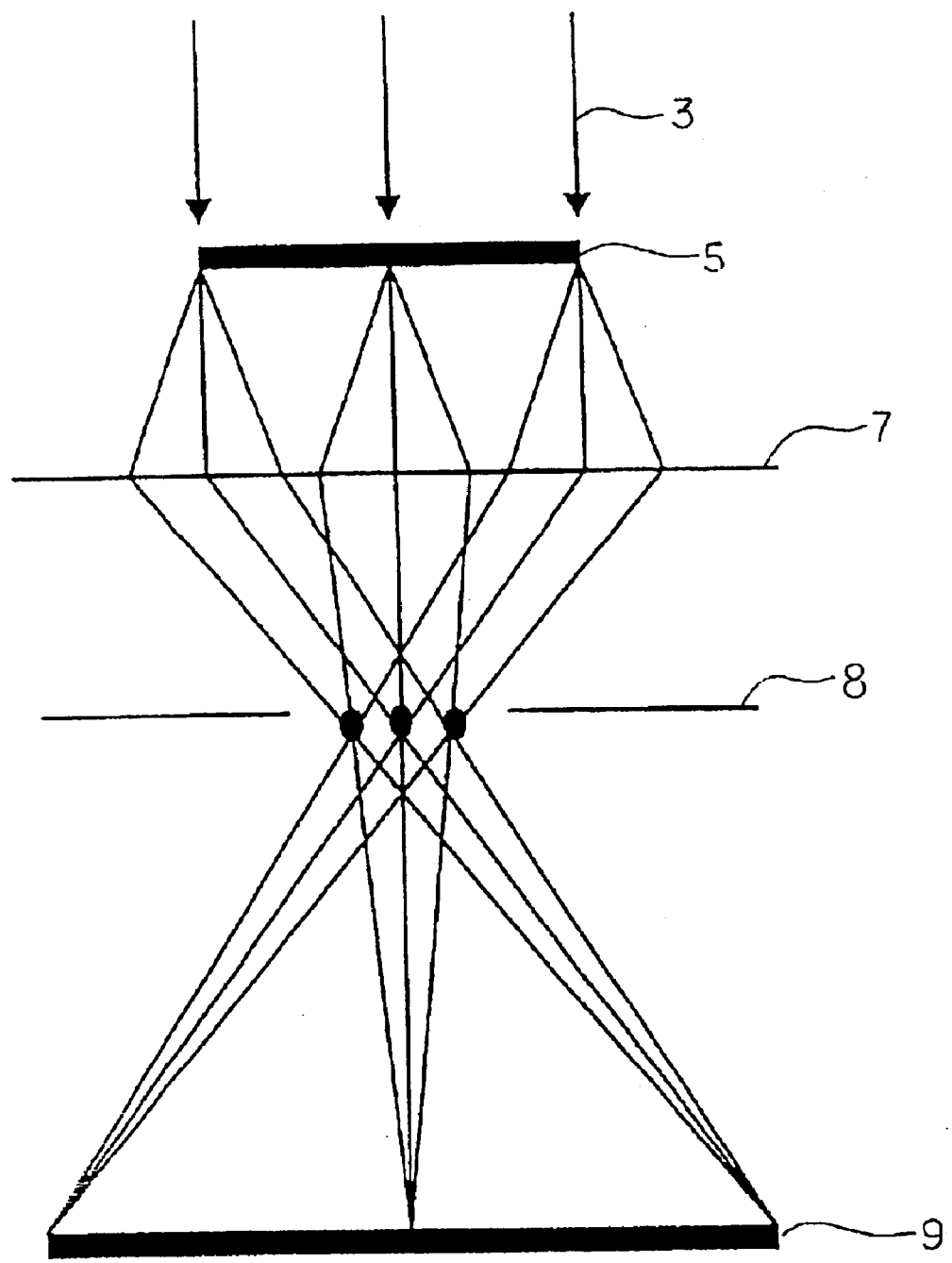
FIG. 7 is a schematic view of a first embodiment of Transmission Electron Microscopy (TEM) according to the present invention.

FIG. 7 shows how an interference image is made by the phase difference. As shown in FIG. 7, the image is formed by the phase difference between diffracted electron beams and transmitted beams in the plane of projection.

The material (5) with the thickness of a few tens of nanometer is putted in a chamber. Electron beam (3) can transmit this kind of thick material (5). At the same time, the interaction between the material (5) and the transmitted electrons cause the electron beam separated to diffracted beams and transmitted beams.

Transmitted beam and diffracted beam, which were separated during the transmission through the material (5), pass an objective lens (7) and an aperture (8). As a result of the interference with these two beams, the lattice image of crystal structure is formed. In the present invention, the image plane means the plane where transmitted beam and diffracted beam make the lattice image of a crystal structure by their interference during the transmission of material (5). This image formed in the image plane (9) can be magnified, used as it is or contracted by the lens. In the present invention, the pattern is formed using this image.

The distance of the interference fringe is proportional to the spacing of lattice, which is the distance between atoms. As a result, the atomic array can be distinguished by this interference pattern.

In fact, in the practical high resolution TEM, the first interference image which is formed by the objective lens is magnified sequentially by other lens which is located behind the objective lens. As a result, this image which is magnified by several hundreds of thousand can be observed directly. In general, magnification of an objective lens is the range from several decades to several hundreds. For example, when the magnification of an objective lens is one hundred, 3 nm spacing of atomic array is magnified into 30 nm that is a spacing of interference image. When this interference image is magnified or down scaled again by other lens, the image of atomic line and atoms with the range from a few nm to a few tens of nm will be obtained.

The present invention is intended to make the pattern by using the crystal structure of materials. The electron beam is radiated to the sample material which has a crystal structure and is loaded in the chamber. When the electron is transmitted through this sample, the lattice image is formed by the phase contrast method. The phase contrast is generated by the interference between the transmitted electron beam and the diffracted electron beam. By using this lattice image of the crystal structure, the pattern for the fabrication of the functional device can be obtained.

In this embodiment, method for forming a pattern using a crystal structure of a material is to fabricate the semiconductor devices, by placing a material having a crystal structure in the chamber of the TEM, irradiating electron beam, then, forming a lattice image of that material by a method of the phase contrast imaging, and finally forming the pattern in the semiconductor substrate from a lattice image of the material having a crystal structure.

In the present invention, the method to fabricate the pattern is as follows. The lattice image which is formed in the image plane is magnified or down-scaled to the intended size. Then, this image can expose the photoresist which is applied on the semiconductor materials. This image can be formed by using some parts of the lattice image of the sample material loaded in the chamber.

Followed Table 2 shows the various photoresists depending on the resolution using a crystal structure of materials. For example, photoresist like HSQ (Hydrogen Silsesquioxane) can be used if the resolution of e-beam accelerated by 100 kv voltage is less than 15 nm, as clearly shown in J. Vac. Sci. Technol. B 18, 3419 (2000).

Figure 8:
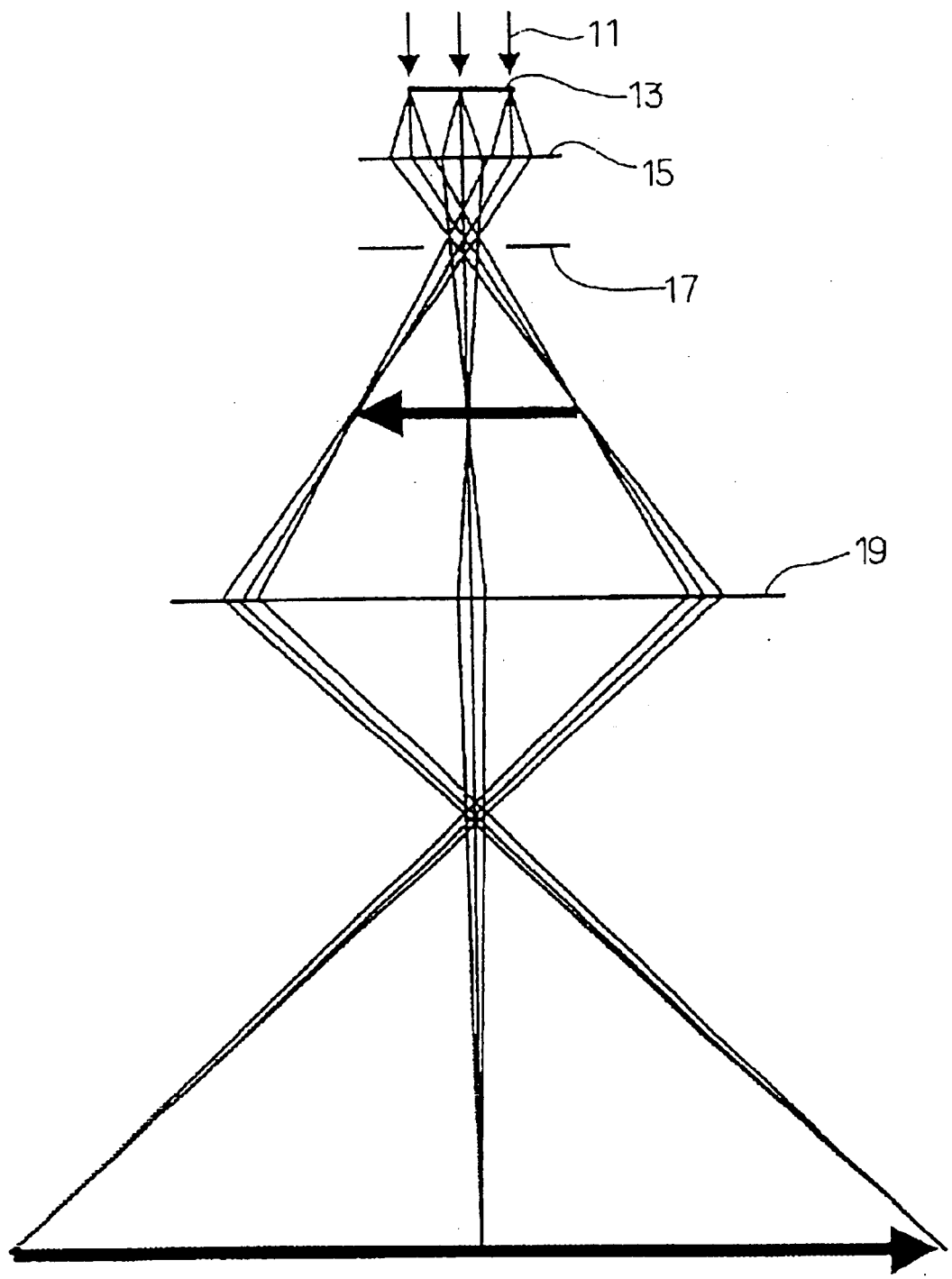
FIG. 8 is a schematic view of a second embodiment of TEM according to the present invention.

FIG. 8 shows another example of the present invention.

As shown in FIG. 8, the material that is processed into the sample with a thickness of a few tens of nanometer (13) is placed at the center of the chamber in order to be passed through by the electron beam (11). The electron beam (11) is split into diffracted beam and transmitted beam by the interaction with the material (13) which have a crystal structure.

Transmitted beam and diffracted beam, into which the incident beam is split during the transmission through the material (13), pass an objective lens (15) and an aperture (17). As a result of the interference with these two beams, the lattice image of crystal structure is formed. In the present invention, the image plane means the plane where transmitted beam and diffracted beam make the lattice image of crystal structure by their interference during the transmission of material (13). The intermediate lens (19) magnifies the image, which is formed at the image plane.

In the present invention, spacing of the atomic plane of a material, alignment of the electron beam, the degree of vacuum in the column of the TEM, the degree of correction of a astigmatism, and the brightness of the electron gun determine the accelerating voltage. Generally, the current accelerating voltage is the range from 100 keV to 1 MeV. If

TABLE 2

| Resist | Vendor | Tone | Resolution | Lithography Equipment | Source |
|---|---|---|---|---|---|
| NEB22 | Sumitomo | Negative | 40 nm in 200 nm film | 50 kV e-beam | Microelectronics Eng., 53, 461 (2000) |
| UVN30 | Shipley | Negative | 50 nm in 200 nm film | 50 kV e-beam | Microelectronics Eng., 53, 461 (2000) |
| AZPN114 | Clariant | Negative | 30 nm in 190 nm film | JBX5DII | J. Vac. Sci. Technol. B, 18, 3143 (2000) |
| ZEP 520 | Nippon Zeon | Positive | 18 nm lines | JBX-9300FS | J. Vac. Sci. Technol. B, 18, 3089 (2000) |
| HSQ | — | Negative | Less than 15 nm | 100 kV e-beam | J. Vac. Sci. Technol. B, 18, 3419 (2000) |
| Calixarene | — | Negative | 12 nm lines | JBX-5FE | J. Vac. Sci. Technol. B, 18, 3424 (2000) |
| PMMA | — | Positive | 19 nm lines | EUV | Microelectronic Eng., 53 13 (2000) |
| UV-6 | — | Positive | 39 nm lines | EUV | Microelectronic Eng., 53 13 (2000) |
| PMMA | — | Positive | 12 nm dots and 20 nm lines | 40 kV e-beam | J. Vac. Sci. Technol. B, 16, 3887 (1998) |

In the high resolution TEM that is used currently, the resolution of the atomic scale is already guaranteed. Therefore, in a method for forming a pattern introduced in the invention, if lattice images of a crystal structure that is formed at the imaging plane is scaled down instead of scaling up, then semiconductor substrate that is applied with the photo resist is exposed to this image. As a result, it is possible to form patterns of a few angstrom on the semiconductor wafer.

The shape of the pattern, which is formed by using a crystal structure of a material by a method of the invention, is determined by a crystal structure of the material used. Therefore, the location of atoms and distances of the atoms in a crystal structure of a material is embodied in the final semiconductor device as it is shaped.

the spacing of the atomic plane is about 3 angstrom, the accelerating voltage of the 100 keV is used, and if the spacing of the atomic plane is about 2 angstrom, the accelerating voltage of the 200 keV is required.

The single electron transistor device, which is fabricated by a method of the invention, has the structure that is constituted by a semiconductor substrate, a source region that is formed in the semiconductor substrate, a drain region spaced from the drain region in the semiconductor substrate, and a layer that includes quantum dots. These quantum dots are placed on the semiconductor region located between the drain region and the source region and have the same pattern with the lattice image of the material in the chamber FIG. 9 shows another example of the present invention.

Figure 9:
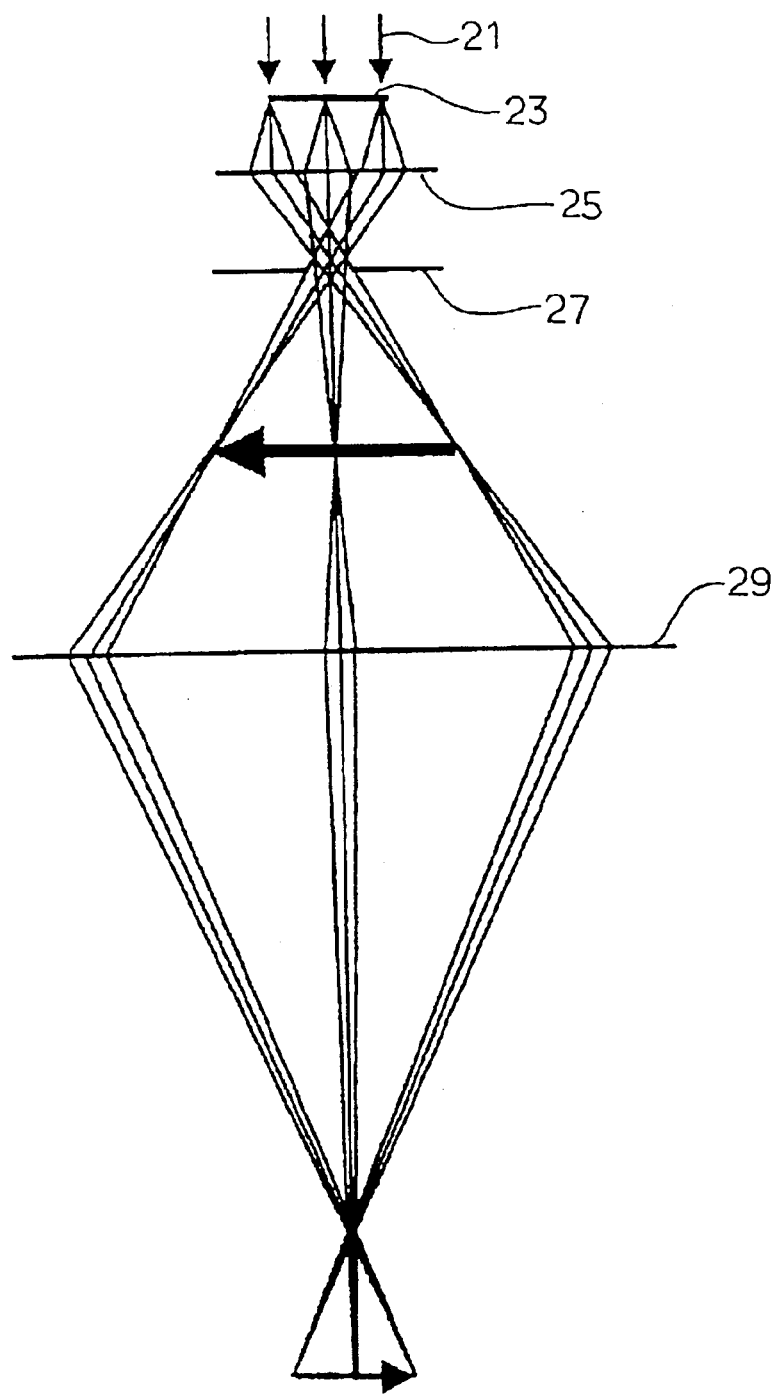
FIG. 9 is a schematic view of a third embodiment of TEM according to the present invention.

As shown in FIG. 9 the sample material (23) of a few tens of nanometer is placed at the center of the chamber in order to be passed through by the electron beam (21). The electron beam (21) is split into diffracted beam and transmitted beam by the interaction with the material (23) which has a crystal structure.

Transmitted beam and diffracted beam, into which the incident beam is split during the transmission through the material (23), pass an objective lens (25) and an aperture (27). As a result of the interference with these two beams, the lattice image of crystal structure is formed. In the present invention, the image plane means the plane where transmitted beam and diffracted beam make the lattice image of crystal structure by their interference during the transmission of the material (23). The intermediate lens (29) can reduce the image, which is formed at the image plane.

Figure 10A:
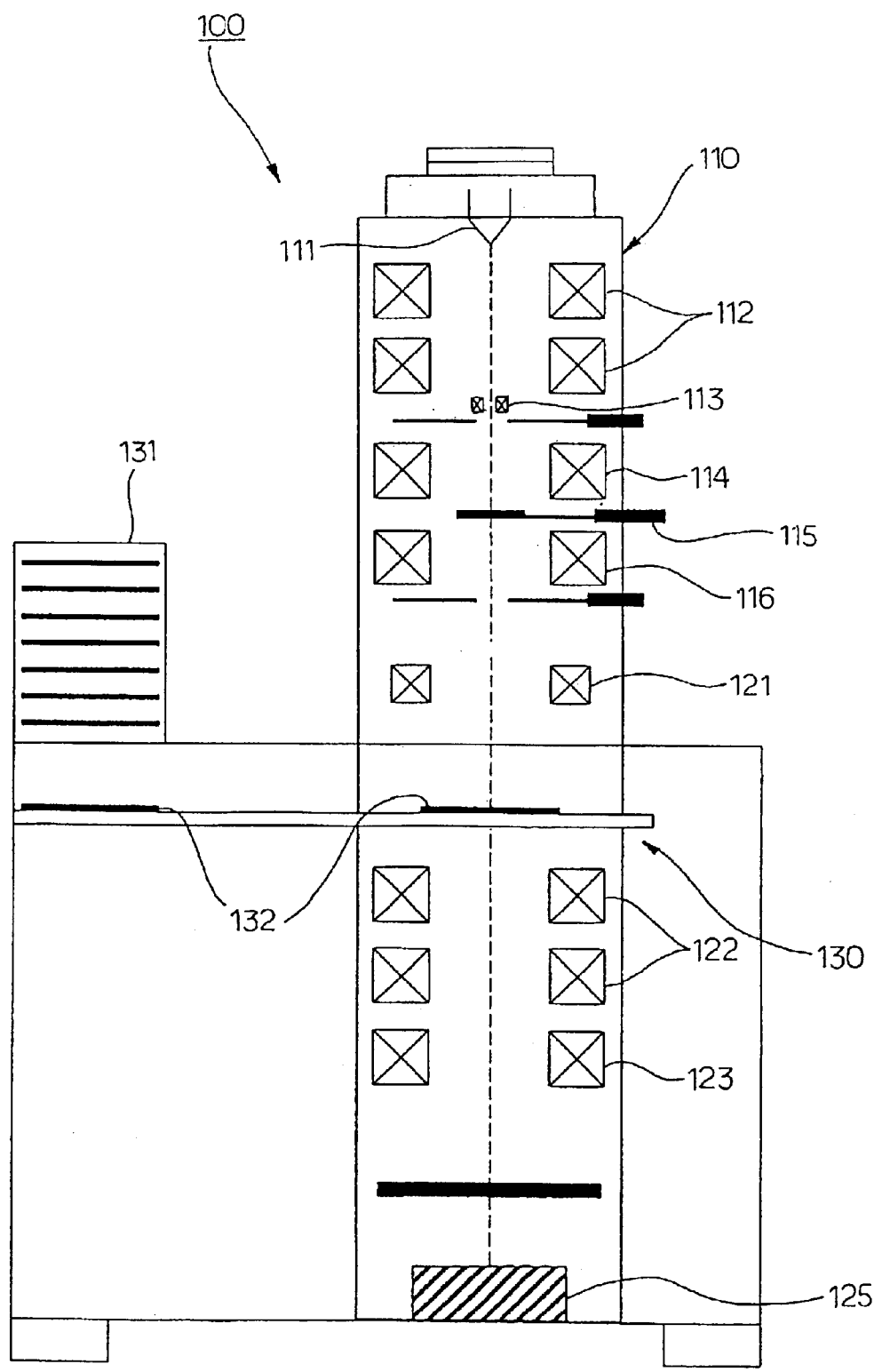
FIGS. 10A and 10B are schematic views of an embodiment of pattern forming apparatus using modified TEM according to the present invention.
Figure 10B:
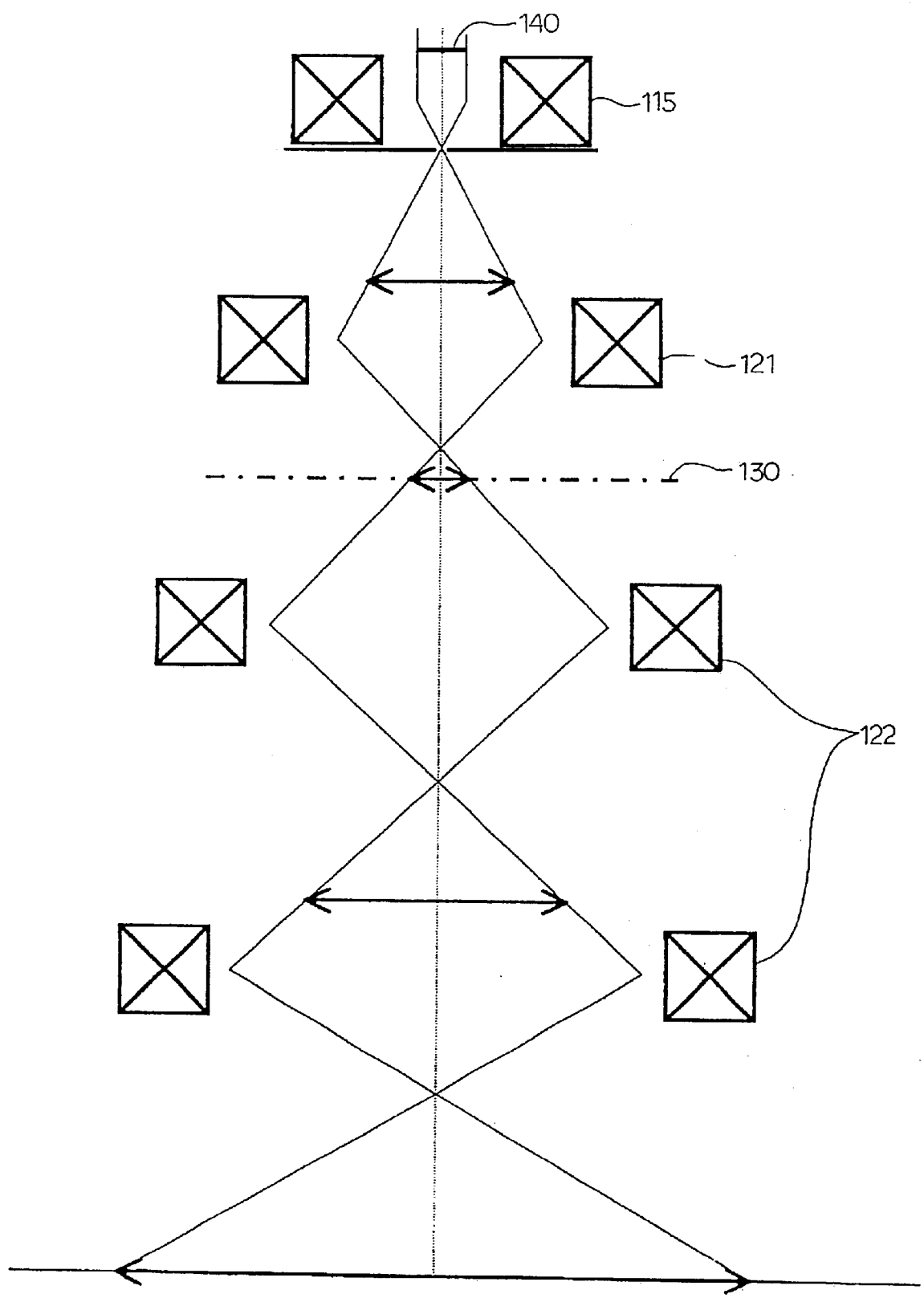

In this embodiment, a construction figure of apparatus for forming a pattern is shown in FIG. 10A and FIG. 10B. The apparatus for forming a pattern in the present invention (100) are composed of modified TEM (110), a wafer-moving device (130) that is equipped with a wafer cassette (131), which is filled with a large number of wafers (132) to form a pattern of a crystal structure of a material that is formed by the TEM (110).

The TEM equipment (110) is composed of an electron gun irradiating the electrons with sufficient energy to pass through a material, a focusing device that focus the electron beam radiated from the electron gun (111), additive focusing device that focus the electron beam on the uniform spot, a loading means (115) that loads the material that electron beam passes through, an objective lens (116) to form lattice images by transmitted and diffracted beam split during passing through the material, a number of lenses to magnify or shrink images formed by the objective lens (121, 122, 123), and wafer-moving device equipped with wafers (132) that can be formed a desired size of the pattern from a lattice image.

The condenser lens (112) can be used as the focusing device and objective lens (114) can be used as an additive focusing device. In addition, pattern lens (121), intermediate lens (122), and projection lens (123) can be used as a number of lenses in turn or alteration.

Furthermore, the wafer-moving device can be inserted as the form of the wafer cassette loaded with a number of wafers (132), between the a number of lenses (121, 122, 123). The wafers have been applied with photoresist after deposition of gate oxide and amorphous silicon on the substrate in which source and drain regions are already formed (as shown in FIG. 12C).

Figure 11A:
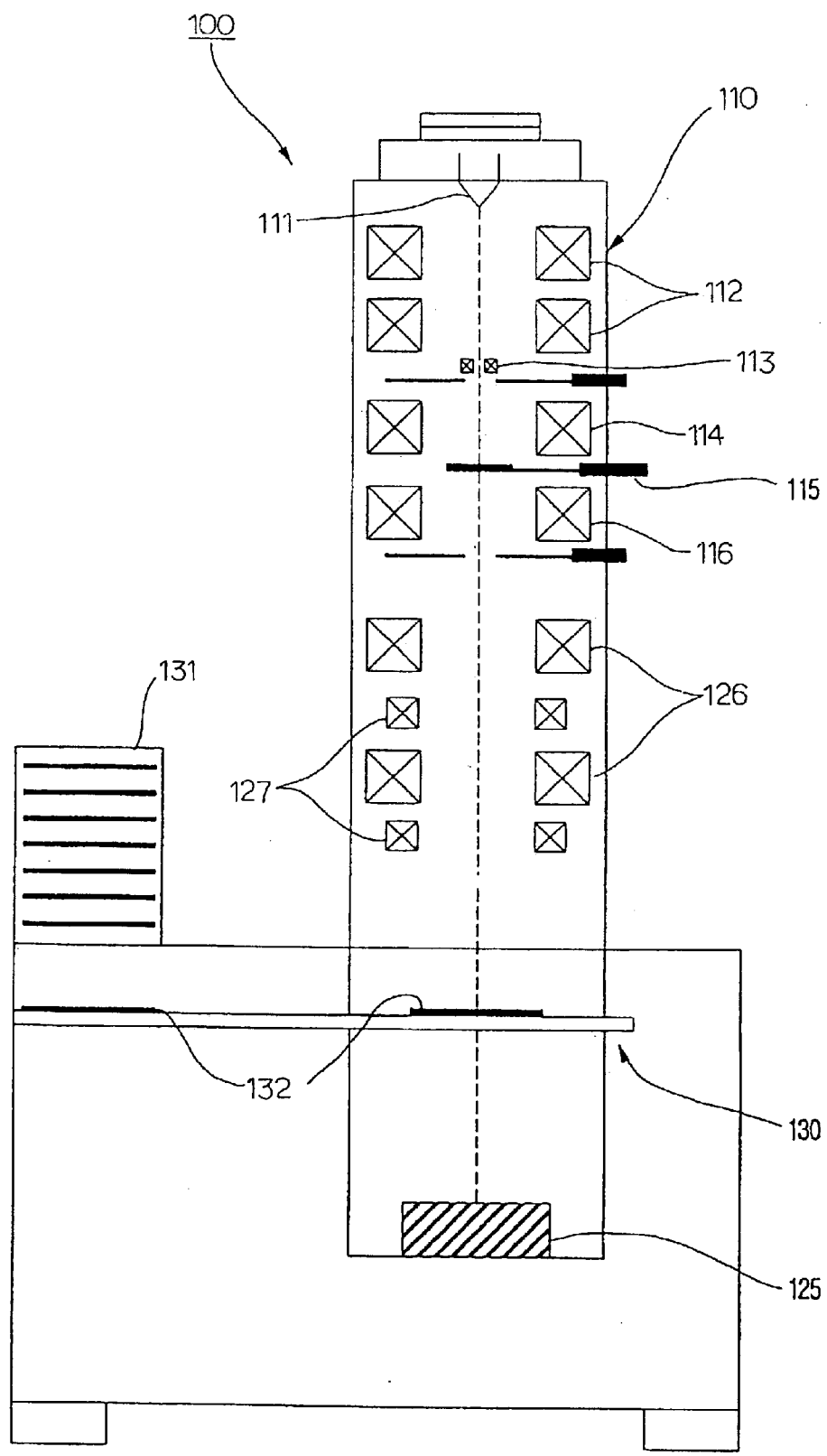
FIGS. 11A and 11B are schematic views of another embodiment of pattern forming apparatus using modified TEM according to the present invention.
Figure 11B:
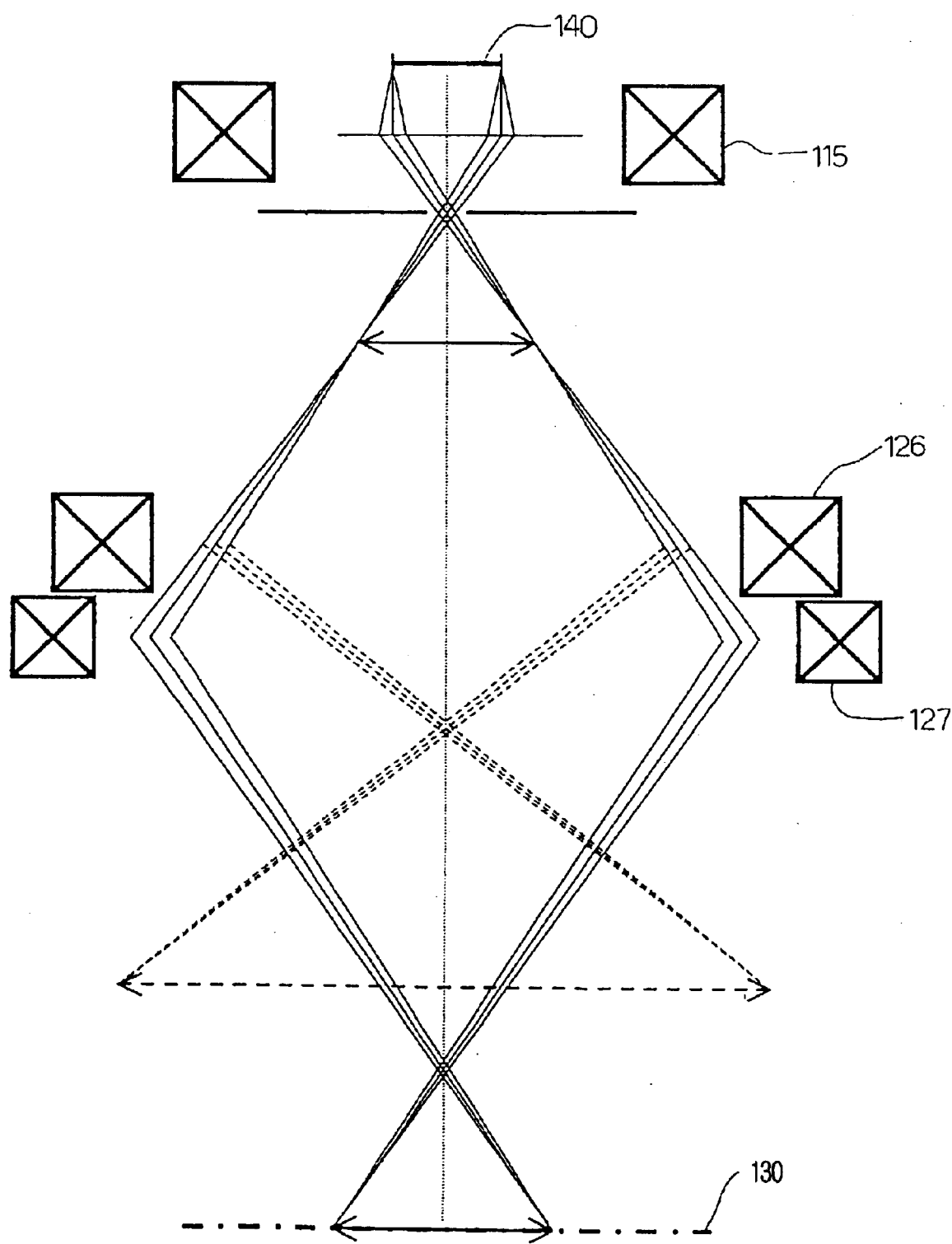

FIG. 10A and FIG. 10B illustrate the constructions of the formation of pattern, which is relatively smaller than FIG. 11A and FIG. 11B illustrate, on the wafer. In FIG. 10A and FIG. 10B, the pattern lens (121) controls the magnification of an image generated by the objective (115) lens (e.g. an image is magnified 20 times), and an image is magnified 100,000 times by the one or more intermediate lenses (122). For example, if the image are wanted to magnify from 10 to 100 times, i.e. the image are desired to be magnified 10 times, an image formed at an imaging plane of the objective lens must be scaled-down by half using the pattern lens (121). And if the image are desired to be magnified 100 times, an image formed at the imaging plane of the objective lens must be magnified by 5 times using pattern lens (121).

That is, after controlling the focus of the image etc. at magnification of the 10,0000, pattern is formed by inserting the wafer (132) in the imaging plane of the pattern lens using the wafer-moving device.

FIG. 11A is a figure of apparatus for forming a pattern using TEM and FIG. 11B is a schematic diagram of FIG. 11A, which illustrates the formation of the relatively larger pattern than FIG. 10A and FIG. 10B illustrate, on the wafer.

As shown in FIG. 11A and FIG. 11B, an image generated by the objective lens (115) is magnified by 100,000, then an exact phase contrast is get by the CCD detector (125), and the desired size of pattern (e.g. magnification of 10 to 100) are formed on the wafer (132) by operating pattern lens (127) which is set to the desired magnification, after the current of the intermediate lens (126) is off.

That is, the size of a pattern can be controlled by locating the wafer (132), which is moved by the wafer-moving device (130), between the groups of the lenses (pattern lens and intermediate lens) (126, 127).

Process to fabricate single electron transistor using apparatus, shown in FIG. 10A or FIG. 11A, are illustrated from FIG. 12A to FIG. 12F.

FIGS. 12A to 12F are sectional views sequentially illustrating an embodiment of a process of fabricating a single electron transistor.

Figure 12A:
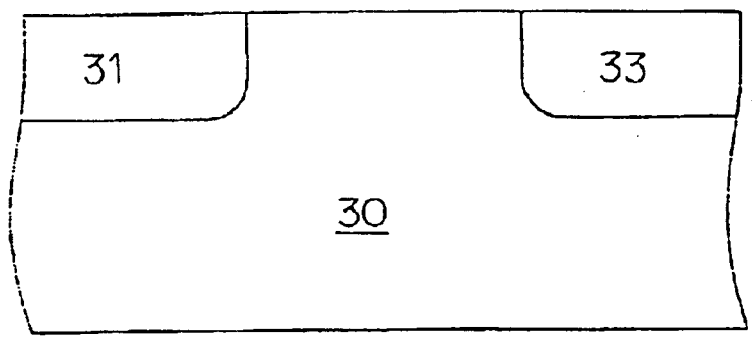
FIGS. 12A to 12F are sectional views sequentially illustrating an embodiment of a process of fabricating single electron transistor.

FIG. 12A illustrates the steps of forming a source (31) and a drain region (33) in Si wafer.

Figure 12B:
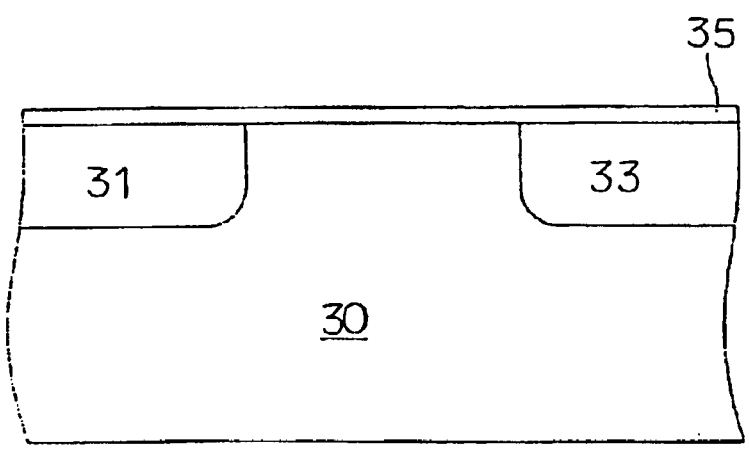
Figure 12C:
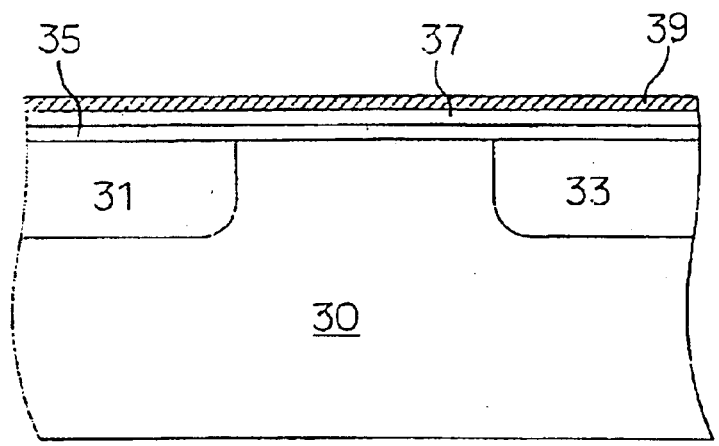

FIG. 12B illustrates the steps of growing a gate oxide film (35) of a few nm thickness on the Si wafer and depositing the amorphous Si (37) of a few nm thickness on the gate oxide (35).

FIG. 12C illustrates the steps of coating photo-resist (39) on the amorphous Si (37).

Then place a silicon having [110] zone axis in the TEM chamber to form the pattern as shown in FIG. 5E.

Figure 12D:
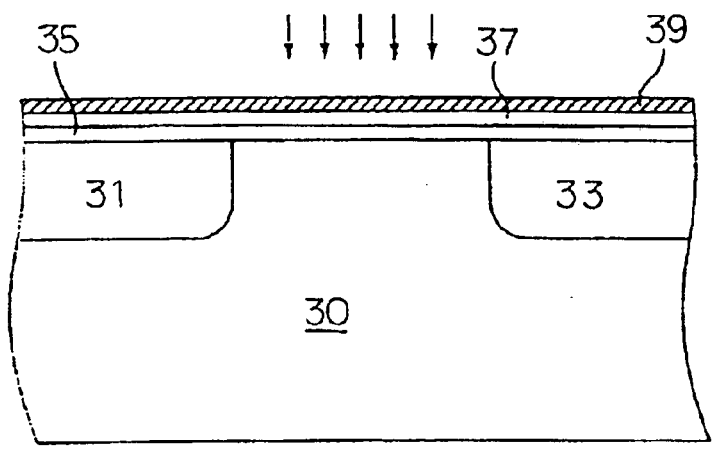

FIG. 12D illustrates the steps of radiating the electron beam to expose the photo-resist film (39).

Figure 12E:
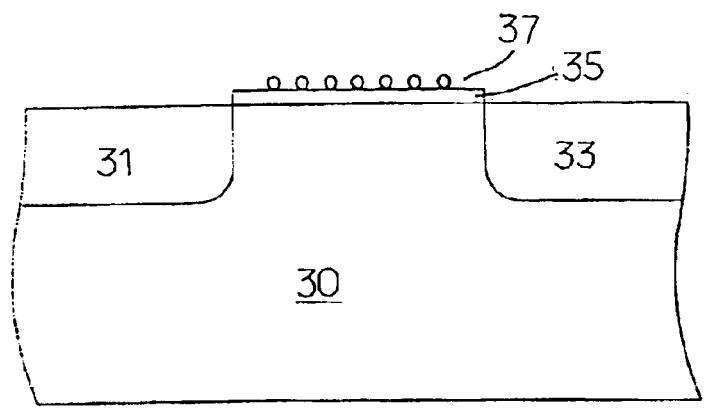

FIG. 12E illustrates the steps of removing the photo-resist film (39), and etching the amorphous silicon (37) using the plasma process to form quantum dots.

Figure 12F:
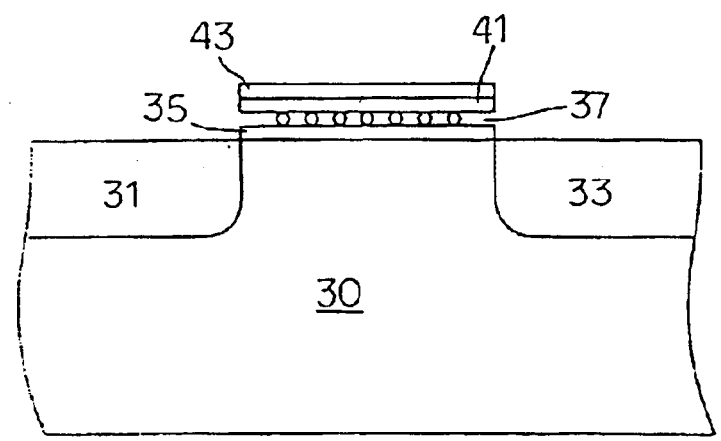

FIG. 12F illustrates the steps of depositing control oxide (41) and poly-silicon (43) on the amorphous silicon (37) on that region formed quantum dots and then patterning. As a result, the single electron transistor device is fabricated In the fabricated device, the pattern of quantum dot that is made on the gate oxide (35) is the same with the pattern of Si, which has [110] zone axis. The size of quantum dot is 5 nm, and the density is about 10 exp $12/cm^2$.

In accordance with the present invention as described above, the quantum dots can be formed and controlled using the lattice image of a crystal structure.

While the present invention has been described in detail with reference to the specific embodiments, they are mere exemplary applications. Thus, it is to be clearly understood that many variations can be made by anyone skilled in the art within the scope and spirit of the present invention.

What is claimed is:

1. An apparatus for forming a pattern using a crystal structure of a material which is modified from a Transmission Electron Microscopy (TEM), comprising:

an electron gun for radiating electrons to pass through said material;

a first means for focusing said electrons radiated by said electron gun;

a second means for focusing said electrons on a uniform spot;

a loading means for loading said material which is passed through by said electrons;

a forming means for forming a lattice image using a diffracted beam and a transmitted beam split during passing through said material;

a plurality of lenses for scaling up or down said lattice image formed by said forming means; and an irradiated material mover for inserting said irradiated material between or below said plurality of lenses for making the formation of said lattice image of predetermined size.

2. The apparatus of claim 1, wherein said lattice image is formed by a method of the phase contrast imaging.

3. The apparatus of claim 1, wherein said material having a crystal structure is processed into a thickness of a few tens of nanometer.

4. The apparatus of claim 1, wherein said irradiated material is a semiconductor substrate.

5. The apparatus of claim 3, wherein said irradiated material mover is a wafer mover comprising a wafer cassette installed a plurality of wafers and inserts said wafer between said plurality of lenses.

6. The apparatus of claim 3, wherein said semiconductor substrate has been applied with photo-resist film after deposition of gate oxide and amorphous silicon on the substrate in which source and drain regions are already formed.

7. The apparatus of claim 1, wherein said first means for focusing is a condenser lens.

8. The apparatus of claim 1, wherein said second means for focusing is an objective lens.

9. An apparatus for forming a pattern using a crystal structure of a material which is modified from a Transmission Electron Microscopy (TEM), comprising:
   an electron gun for radiating electrons to pass through said material;
   a means for focusing said electrons radiated by said electron gun on a uniform spot;
   a loading means for loading said material which is passed through by said electrons;
   a forming means for forming a lattice image using a diffracted beam and a transmitted beam split during passing through said material;
   a plurality of lenses for scaling up or down said lattice image formed by said forming means; and
   an irradiated material mover for inserting said irradiated material between or below said plurality of lenses for making the formation of said lattice image of predetermined size.

10. The apparatus of claim 9, wherein said lattice image is formed by a method of the phase contrast imaging.

11. The apparatus of claim 9, wherein said irradiated material is a semiconductor substrate.

12. The apparatus of claim 9, wherein said irradiated material mover is a wafer mover comprising a wafer cassette installed a plurality of wafers and inserts said wafer between said plurality of lenses.

13. The apparatus of claim 9, wherein said semiconductor substrate has been applied with photo-resist film after deposition of gate oxide and amorphous silicon on the substrate in which source and drain regions are already formed.

14. A method for forming a pattern using a crystal structure of a material as a mask, comprising the steps of:
    locating said material having a crystal structure in the chamber of the modified TEM (transmission electron microscopy);
    radiating an electron beam to said material in said modified TEM (transmission electron microscopy);
    forming a pattern from a lattice image of said material formed as a result of interference between diffracted electron beams and transmitted electron beams passed through said material on the surface of an irradiated material.

15. The method of claim 14, wherein said lattice image of material is formed by a method of the phase contrast imaging.

16. The method of claim 14, wherein said irradiated material is a photoresist material.

17. A method for forming a quantum dot using a crystal structure of a material as a mask, comprising the steps of:
    locating said material having a crystal structure in the chamber of the modified TEM (transmission electron microscopy);
    radiating an electron beam to said material in said modified transmission electron microscopy;
    forming a pattern from a lattice image of said material formed as a result of interference between diffracted electron beams and transmitted electron beams passed through said material on the surface of a photoresist material on a material on the semiconductor substrate,
    patterning said photoresist material,
    etching said material on the semiconductor substrate using a plasma process.

18. The method of claim 17, wherein said lattice image of material is formed by a method of the phase contrast imaging.

19. A semiconductor device, comprising:
    a semiconductor substrate;
    a source region located in said semiconductor substrate;
    a drain region spaced from said source region and located in said semiconductor substrate;
    a quantum dot layer on a semiconductor substrate region which is located between said source and drain region and formed by patterning a silicon layer using a crystal structure of material as a patterning mask.

20. The semiconductor device of claim 19, wherein said lattice image of material is formed by a method of the phase contrast imaging.

* * * * *

UNITED STATES PATENT AND TRADEMARK OFFICE
CERTIFICATE OF CORRECTION

PATENT NO. : 6,855,481 B2
APPLICATION NO. : 10/220364
DATED : February 15, 2005
INVENTOR(S) : Kim It is certified that error appears in the above-identified patent and that said Letters Patent is hereby corrected as shown below:

On the title page, item (56), under "U.S. Patent Documents", in column 2, line 1, below "438/694" insert -- 5,079,112    1/1992 Berger et al. ……………...430/4 --.

On the title page, item (56), under "U.S. Patent Documents", in column 2, line 1, below "438/694" insert -- 5,130,213    7/1992 Berger et al. ……………….430/4 --.

On the title page, item (56), under "U.S. Patent Documents", in column 2, line 1, below "438/694" insert -- 5,258,246    11/1993 Berger et al. ……………..430/4 --.

On the title page, item (56), under "U.S. Patent Documents", in column 2, line 1, below "438/694" insert -- 5,532,184    7/1996 Kato ………..437/133 --.

On the title page, item (56), under "U.S. Patent Documents", in column 2, line 1, below "438/694" insert -- 5,767,521    6/1996 Takeno et al. ……………..250/492 --.

On the title page, item (56), under "U.S. Patent Documents", in column 2, line 1, below "438/694" insert -- 6,159,620    12/2000 Heath et al. ……………..428/615 --.

On the title page, item (56), under "U.S. Patent Documents", in column 2, line 2, below "438/22" insert -- 6,211,013    4/2001 Park et al. ………………..438/257 --.

On the title page, item (56), under "U.S. Patent Documents", in column 2, line 2, below "438/22" insert -- 6,335,425    1/2002 Park et al. ………………..438/257 --.

On the title page, item (56), under "U.S. Patent Documents", in column 2, line 2, below "438/22" insert -- 6,342,716    1/2002 Morita et al. ……………...257/315 --.

On the title page, item (56), under "U.S. Patent Documents", in column 2, line 4, below "257/321" insert -- 2003/0052342    3/2003 Kim ……………..257/213 --.

On the title page, item (56), under "Foreign Patent Documents", in column 2, line 2, below "4/1999" insert -- JP 11266004 A 9/1999 --.

On the title page, item (56), under "Foreign Patent Documents", in column 2, line 3, below "6/2000" insert -- JP 11329959 11/2000 --.

On the title page, item (56), under "Foreign Patent Documents", in column 2, line 3, below "6/2000" insert -- JP 2000-307097 11/2000 --.

UNITED STATES PATENT AND TRADEMARK OFFICE
CERTIFICATE OF CORRECTION

PATENT NO. : 6,855,481 B2
APPLICATION NO. : 10/220364
DATED : February 15, 2005
INVENTOR(S) : Kim It is certified that error appears in the above-identified patent and that said Letters Patent is hereby corrected as shown below:

On the title page, item (57), under "Abstract", in column 2, lines 4-5, delete "with 1~50 nm dimension" and insert -- having a nano or tens of nano meter order --, therefor.

On the title page, item (57), under "Abstract", in column 2, line 5, after "array of a" insert -- single or a poly --.

On the title page, item (57), under "Abstract", in column 2, line 7, after "structure." insert -- The electron beam lithography method in accordance with the present invention uses the phase contrast atomic image of a single or a poly crystalline material itself. --.

On the title page, item (57), under "Abstract", in column 2, line 7, below "structure." delete "In the present invention, the functional device means an electronic, magnetic, or optical device that can be fabricated by procedures including the formation process of quantum dots or wires.".

In column 1, line 12, delete "with 1~50 nm dimension" and insert -- having a nano or tens of nano meter order --, therefor.

In column 1, line 13, after "array of a" insert -- single or a poly --.

In column 1, line 15, after "structure." insert -- The electron beam lithography method in accordance with the present invention uses the phase contrast atomic image of a single or a poly crystalline material itself. --.

In column 1, line 60, after "of a" insert -- single or a poly crystalline --.

In column 1, line 64, after "of a" insert -- single or a poly crystalline --.

In column 2, line 1, after "of a" insert -- single or a poly crystalline --.

In column 2, line 12, after "of a" insert -- single or a poly crystalline --.

In column 2, line 28, after "material is" insert -- an electron beam resist deposited on --.

In column 2, line 36, delete "photo-resist film" and insert -- electron beam resist deposited on --, therefor.

In column 2, line 40, after "of a" insert -- single or a poly crystalline --.

UNITED STATES PATENT AND TRADEMARK OFFICE
CERTIFICATE OF CORRECTION

| | | |
|---|---|---|
| PATENT NO. | : 6,855,481 B2 | |
| APPLICATION NO. | : 10/220364 | |
| DATED | : February 15, 2005 | |
| INVENTOR(S) | : Kim | |

It is certified that error appears in the above-identified patent and that said Letters Patent is hereby corrected as shown below:

In column 2, line 48, delete "material." and insert -- material such as an electron beam resist. --, therefor.

In column 2, line 51, after "having" insert -- a --.

In column 2, line 53-54, delete "a photoresist material" and insert -- an electron beam resist deposited --, therefor.

In column 2, line 56, delete "photoresist material" and insert -- electron beam resist deposited on --, therefor.

In column 5, line 60, delete "simple cubic lattice" and insert -- face centered cubic crystal structure --, therefor.

In column 6, line 3, after "quantum" insert -- dot and --.

In column 6, line 55, delete "3 nm" and insert -- 0.3 nm --, therefor.

In column 6, line 62, delete "materials." and insert -- a single or a poly crystalline sample material. --, therefor.

In column 7, line 5, after "of a" insert -- single or a poly crystalline --.

In column 7, line 6, after "placing a" insert -- single or a poly crystalline --.

In column 7, line 15, delete "photoresist" and insert -- electron beam resist --, therefor.

In column 7, line 19, delete "Followed" and insert -- Following --, therefor.

In column 7, line 19, delete "photoresists" and insert -- electron beam resists --, therefor.

In column 7, line 21, delete "photoresist" and insert -- electron beam resist --, therefor.

In column 7, lines 57-58, delete "down instead of scaling up" and insert -- up or down to the desired magnification --, therefor.

In column 7, line 59, delete "photo resist" and insert -- electron beam resist --, therefor.

In column 7, line 60, delete "angstrom" and insert -- nanometers --, therefor.

UNITED STATES PATENT AND TRADEMARK OFFICE
CERTIFICATE OF CORRECTION

| | | |
|---|---|---|
| PATENT NO. | : 6,855,481 B2 | Page 4 of 7 |
| APPLICATION NO. | : 10/220364 | |
| DATED | : February 15, 2005 | |
| INVENTOR(S) | : Kim | |

It is certified that error appears in the above-identified patent and that said Letters Patent is hereby corrected as shown below:

In column 7, line 60, delete "semiconductor wafer." and insert -- substrate. --, therefor.

In column 7, line 63, after "of a" insert -- single or a poly crystalline --.

In column 7, line 66, after "of" delete "a" and insert -- the --, therefor.

In column 8, line 2, after "FIG. 8," delete "the" and insert -- a single or a poly crystalline --, therefor.

In column 8, line 66, delete "FIG. 9 the" and insert -- FIG. 9, a single or a poly crystalline --, therefor.

In column 9, line 44, delete "photoresist" and insert -- electron beam resist --, therefor.

In column 9, line 67, after "using" insert -- a modified --.

In column 10, line 25, delete "photo-resist" and insert -- electron beam resist --, therefor.

In column 10, line 30, delete "photo-resist" and insert -- electron beam resist --, therefor.

In column 10, line 31, delete "photo-resist" and insert -- electron beam resist --, therefor.

In column 10, line 44, after "of a" insert -- single or a poly crystalline --.

Delete Issued Patent Claims 1-20 and insert the following Claim Set therefor.

1. An apparatus for forming a pattern using a crystal structure of a single or a poly crystalline material which is modified from a Transmission Electron Microscopy(TEM), comprising: an electron gun for radiating electrons to pass through said material; a first means for focusing said electrons radiated by said electron gun on a uniform spot; a loading means for loading said material which is passed through by said electrons; a forming means for forming a pattern from a lattice image of said material formed as a result of interference between diffracted beam and transmitted beam passed through said material; and an irradiated material mover for inserting a irradiated material on which said pattern if formed.

UNITED STATES PATENT AND TRADEMARK OFFICE
CERTIFICATE OF CORRECTION

PATENT NO. : 6,855,481 B2
APPLICATION NO. : 10/220364
DATED : February 15, 2005
INVENTOR(S) : Kim It is certified that error appears in the above-identified patent and that said Letters Patent is hereby corrected as shown below:

2. The apparatus of claim 2 further comprising a second means for focusing said electrons on a uniform spot below said first means for focusing.

3. The apparatus of claim 1, further comprising a plurality of lenses for scaling up or down said lattice image formed by said forming means wherein said irradiated material mover for inserting said irradiated material between or below said plurality of lenses for making the formation of said lattice of predetermined size.

4. The apparatus of claim 1, wherein said irradiated material is an electron beam resist deposited on substrate.

5. The apparatus of claim 1, wherein said material having a crystal structure is processed into a thickness of a few tens of manometer.

6. The apparatus of claim 3, wherein said irradiated material mover is a wafer mover comprising a wafer cassette installed a plurality of wafers and inserts said wafer between said plurality of lenses.

7. The apparatus of claim 1, wherein said first means for focusing is a condenser lens.

8. The apparatus of claim 2, wherein said second means for focusing is an objective lens.

9. An apparatus for forming a pattern using a crystal structure of a single or a poly crystalline material which is modified from a Transmission Electron Microscopy(TEM), comprising: an electron gun for radiating electrons to pass through said material; a first means for focusing said electrons radiated by said electron; a second means for focusing said electrons on a uniform spot; a loading means for loading said material which is passed through by said electrons; a forming means for forming a lattice image using a diffracted beam and a transmitted beam split during passing through said material; a plurality of lenses for scaling up or down said lattice image formed by said forming means; and an irradiated material mover for inserting said irradiated material between or below said plurality of lenses for making the formation of said lattice image of predetermined size.

10. The apparatus of claim 9, wherein said lattice image is formed by a method of the phase contrast imaging.

UNITED STATES PATENT AND TRADEMARK OFFICE
CERTIFICATE OF CORRECTION

| | |
|---|---|
| PATENT NO. | : 6,855,481 B2 |
| APPLICATION NO. | : 10/220364 |
| DATED | : February 15, 2005 |
| INVENTOR(S) | : Kim |

It is certified that error appears in the above-identified patent and that said Letters Patent is hereby corrected as shown below:

11. The apparatus of claim 9, wherein said irradiated material is a semiconductor substrate.

12. The apparatus of claim 9, wherein said irradiated material mover is a wafer mover comprising a wafer cassette installed a plurality of wafers and inserts said wafer between said plurality of lenses.

13. The apparatus of claim 9, wherein said semiconductor substrate has been applied with electron beam resist film after deposition of gate oxide and amorphous silicon on the substrate in which source and drain regions are already formed.

14. A method for forming a pattern using a crystal structure of a single or a poly crystalline material as a mask, comprising the steps of: locating said material having a crystal structure in the chamber of the modified TEM(transmission electron microscopy); radiating an electron beam to said material in said modified TEM(transmission electron microscopy); forming a pattern from a lattice image of said material formed as a result of interference between diffracted electron beams and transmitted electron beams passed through said material; and scaling up or scaling down said pattern on the surface of an irradiated material.

15. The method of claim 14, wherein said lattice image of material is formed by a method of the phase contrast imaging.

16. The method of claim 14, wherein said irradiated material is an electron beam resist material.

17. A method for forming a quantum dot using a crystal structure of a single or a poly crystalline material as a mask, comprising the steps of: locating said material having a crystal structure in the chamber of the modified TEM (transmission electron microscopy); radiating an electron beam to said material in said modified transmission electron microscopy; forming a pattern from a lattice image of said material formed as a result of interference between diffracted electron beams and transmitted electron beams passed through said material; scaling up or scaling down said pattern on the surface of an electron beam resist on a substrate, patterning said electron beam resist.

18. The method of claim 17, wherein said lattice image of material is formed by a method of the phase contrast imaging.

UNITED STATES PATENT AND TRADEMARK OFFICE
CERTIFICATE OF CORRECTION

PATENT NO. : 6,855,481 B2
APPLICATION NO. : 10/220364
DATED : February 15, 2005
INVENTOR(S) : Kim It is certified that error appears in the above-identified patent and that said Letters Patent is hereby corrected as shown below:

19. A semiconductor device, comprising: a semiconductor substrate; a source region located in said semiconductor substrate; a drain region spaced from said source region and located in said semiconductor substrate; a quantum dot layer on a semiconductor substrate region which is located between said source and
drain region and formed by patterning a gate layer using a single or a ploy crystalline material as a mask, said patterning is comprising the steps of: locating said material having a crystal structure in the chamber of the modified TEM(transmission electron microscopy); radiating an electron beam to said material in said modified transmission electron microscopy; forming a pattern from a lattice image of said material formed as a result of interference between diffracted electron beams and transmitted electron beams passed through said material; scaling up or scaling down said pattern on the surface of an electron beam resist on said gate layer, patterning said electron beam resist.

20. The semiconductor device of claim 19, wherein said lattice image of material is formed by a method of the phase contrast imaging.

Signed and Sealed this

Thirtieth Day of December, 2008

JON W. DUDAS
*Director of the United States Patent and Trademark Office*

UNITED STATES PATENT AND TRADEMARK OFFICE
CERTIFICATE OF CORRECTION

PATENT NO.       : 6,855,481 B2
APPLICATION NO. : 10/220364
DATED            : February 15, 2005
INVENTOR(S)      : Kim It is certified that error appears in the above-identified patent and that said Letters Patent is hereby corrected as shown below:

On the title page, item (56), under "U.S. Patent Documents", in column 2, line 1, below "438/694" insert -- 5,079,112    1/1992 Berger et al. ……………...430/4 --.

On the title page, item (56), under "U.S. Patent Documents", in column 2, line 1, below "438/694" insert -- 5,130,213    7/1992 Berger et al. ……………….430/4 --.

On the title page, item (56), under "U.S. Patent Documents", in column 2, line 1, below "438/694" insert -- 5,258,246    11/1993 Berger et al. ……………..430/4 --.

On the title page, item (56), under "U.S. Patent Documents", in column 2, line 1, below "438/694" insert -- 5,532,184    7/1996 Kato ………..437/133 --.

On the title page, item (56), under "U.S. Patent Documents", in column 2, line 1, below "438/694" insert -- 5,767,521    6/1996 Takeno et al. …………….250/492 --.

On the title page, item (56), under "U.S. Patent Documents", in column 2, line 1, below "438/694" insert -- 6,159,620    12/2000 Heath et al. ……………..428/615 --.

On the title page, item (56), under "U.S. Patent Documents", in column 2, line 2, below "438/22" insert -- 6,211,013    4/2001 Park et al. ………………..438/257 --.

On the title page, item (56), under "U.S. Patent Documents", in column 2, line 2, below "438/22" insert -- 6,335,425    1/2002 Park et al. ………………..438/257 --.

On the title page, item (56), under "U.S. Patent Documents", in column 2, line 2, below "438/22" insert -- 6,342,716    1/2002 Morita et al. ………………257/315 --.

On the title page, item (56), under "U.S. Patent Documents", in column 2, line 4, below "257/321" insert -- 2003/0052342    3/2003 Kim ………………257/213 --.

On the title page, item (56), under "Foreign Patent Documents", in column 2, line 2, below "4/1999" insert -- JP 11266004 A 9/1999 --.

On the title page, item (56), under "Foreign Patent Documents", in column 2, line 3, below "6/2000" insert -- JP 11329959 11/2000 --.

On the title page, item (56), under "Foreign Patent Documents", in column 2, line 3, below "6/2000" insert -- JP 2000-307097 11/2000 --.

UNITED STATES PATENT AND TRADEMARK OFFICE
CERTIFICATE OF CORRECTION

PATENT NO.        : 6,855,481 B2
APPLICATION NO.   : 10/220364
DATED             : February 15, 2005
INVENTOR(S)       : Kim It is certified that error appears in the above-identified patent and that said Letters Patent is hereby corrected as shown below:

On the title page, item (57), under "Abstract", in column 2, lines 4-5, delete "with 1~50 nm dimension" and insert -- having a nano or tens of nano meter order --, therefor.

On the title page, item (57), under "Abstract", in column 2, line 5, after "array of a" insert -- single or a poly --.

On the title page, item (57), under "Abstract", in column 2, line 7, after "structure." insert -- The electron beam lithography method in accordance with the present invention uses the phase contrast atomic image of a single or a poly crystalline material itself. --.

On the title page, item (57), under "Abstract", in column 2, line 7, below "structure." delete "In the present invention, the functional device means an electronic, magnetic, or optical device that can be fabricated by procedures including the formation process of quantum dots or wires.".

In column 1, line 12, delete "with 1~50 nm dimension" and insert -- having a nano or tens of nano meter order --, therefor.

In column 1, line 13, after "array of a" insert -- single or a poly --.

In column 1, line 15, after "structure." insert -- The electron beam lithography method in accordance with the present invention uses the phase contrast atomic image of a single or a poly crystalline material itself. --.

In column 1, line 60, after "of a" insert -- single or a poly crystalline --.

In column 1, line 64, after "of a" insert -- single or a poly crystalline --.

In column 2, line 1, after "of a" insert -- single or a poly crystalline --.

In column 2, line 12, after "of a" insert -- single or a poly crystalline --.

In column 2, line 28, after "material is" insert -- an electron beam resist deposited on --.

In column 2, line 36, delete "photo-resist film" and insert -- electron beam resist deposited on --, therefor.

In column 2, line 40, after "of a" insert -- single or a poly crystalline --.

UNITED STATES PATENT AND TRADEMARK OFFICE
CERTIFICATE OF CORRECTION

PATENT NO. : 6,855,481 B2
APPLICATION NO. : 10/220364
DATED : February 15, 2005
INVENTOR(S) : Kim It is certified that error appears in the above-identified patent and that said Letters Patent is hereby corrected as shown below:

In column 2, line 48, delete "material." and insert -- material such as an electron beam resist. --, therefor.

In column 2, line 51, after "having" insert -- a --.

In column 2, line 53-54, delete "a photoresist material" and insert -- an electron beam resist deposited --, therefor.

In column 2, line 56, delete "photoresist material" and insert -- electron beam resist deposited on --, therefor.

In column 5, line 60, delete "simple cubic lattice" and insert -- face centered cubic crystal structure --, therefor.

In column 6, line 3, after "quantum" insert -- dot and --.

In column 6, line 55, delete "3 nm" and insert -- 0.3 nm --, therefor.

In column 6, line 62, delete "materials." and insert -- a single or a poly crystalline sample material. --, therefor.

In column 7, line 5, after "of a" insert -- single or a poly crystalline --.

In column 7, line 6, after "placing a" insert -- single or a poly crystalline --.

In column 7, line 15, delete "photoresist" and insert -- electron beam resist --, therefor.

In column 7, line 19, delete "Followed" and insert -- Following --, therefor.

In column 7, line 19, delete "photoresists" and insert -- electron beam resists --, therefor.

In column 7, line 21, delete "photoresist" and insert -- electron beam resist --, therefor.

In column 7, lines 57-58, delete "down instead of scaling up" and insert -- up or down to the desired magnification --, therefor.

In column 7, line 59, delete "photo resist" and insert -- electron beam resist --, therefor.

In column 7, line 60, delete "angstrom" and insert -- nanometers --, therefor.

UNITED STATES PATENT AND TRADEMARK OFFICE
CERTIFICATE OF CORRECTION

| | | |
|---|---|---|
| PATENT NO. | : 6,855,481 B2 | |
| APPLICATION NO. | : 10/220364 | |
| DATED | : February 15, 2005 | |
| INVENTOR(S) | : Kim | |

It is certified that error appears in the above-identified patent and that said Letters Patent is hereby corrected as shown below:

In column 7, line 60, delete "semiconductor wafer." and insert -- substrate. --, therefor.

In column 7, line 63, after "of a" insert -- single or a poly crystalline --.

In column 7, line 66, after "of" delete "a" and insert -- the --, therefor.

In column 8, line 2, after "FIG. 8," delete "the" and insert -- a single or a poly crystalline --, therefor.

In column 8, line 66, delete "FIG. 9 the" and insert -- FIG. 9, a single or a poly crystalline --, therefor.

In column 9, line 44, delete "photoresist" and insert -- electron beam resist --, therefor.

In column 9, line 67, after "using" insert -- a modified --.

In column 10, line 25, delete "photo-resist" and insert -- electron beam resist --, therefor.

In column 10, line 30, delete "photo-resist" and insert -- electron beam resist --, therefor.

In column 10, line 31, delete "photo-resist" and insert -- electron beam resist --, therefor.

In column 10, line 44, after "of a" insert -- single or a poly crystalline --.

Column 10, line 52 thru Column 12, line 50, delete Issued Patent Claims 1-20 and insert the following Claim Set therefor.

1. An apparatus for forming a pattern using a crystal structure of a single or a poly crystalline material which is modified from a Transmission Electron Microscopy(TEM), comprising: an electron gun for radiating electrons to pass through said material; a first means for focusing said electrons radiated by said electron gun on a uniform spot; a loading means for loading said material which is passed through by said electrons; a forming means for forming a pattern from a lattice image of said material formed as a result of interference between diffracted beam and transmitted beam passed through said material; and an irradiated material mover for inserting a irradiated material on which said pattern if formed.

UNITED STATES PATENT AND TRADEMARK OFFICE
CERTIFICATE OF CORRECTION

| | |
|---|---|
| PATENT NO. | : 6,855,481 B2 |
| APPLICATION NO. | : 10/220364 |
| DATED | : February 15, 2005 |
| INVENTOR(S) | : Kim |

It is certified that error appears in the above-identified patent and that said Letters Patent is hereby corrected as shown below:

2. The apparatus of claim 2 further comprising a second means for focusing said electrons on a uniform spot below said first means for focusing.

3. The apparatus of claim 1, further comprising a plurality of lenses for scaling up or down said lattice image formed by said forming means wherein said irradiated material mover for inserting said irradiated material between or below said plurality of lenses for making the formation of said lattice of predetermined size.

4. The apparatus of claim 1, wherein said irradiated material is an electron beam resist deposited on substrate.

5. The apparatus of claim 1, wherein said material having a crystal structure is processed into a thickness of a few tens of manometer.

6. The apparatus of claim 3, wherein said irradiated material mover is a wafer mover comprising a wafer cassette installed a plurality of wafers and inserts said wafer between said plurality of lenses.

7. The apparatus of claim 1, wherein said first means for focusing is a condenser lens.

8. The apparatus of claim 2, wherein said second means for focusing is an objective lens.

9. An apparatus for forming a pattern using a crystal structure of a single or a poly crystalline material which is modified from a Transmission Electron Microscopy(TEM), comprising: an electron gun for radiating electrons to pass through said material; a first means for focusing said electrons radiated by said electron; a second means for focusing said electrons on a uniform spot; a loading means for loading said material which is passed through by said electrons; a forming means for forming a lattice image using a diffracted beam and a transmitted beam split during passing through said material; a plurality of lenses for scaling up or down said lattice image formed by said forming means; and an irradiated material mover for inserting said irradiated material between or below said plurality of lenses for making the formation of said lattice image of predetermined size.

10. The apparatus of claim 9, wherein said lattice image is formed by a method of the phase contrast imaging.

UNITED STATES PATENT AND TRADEMARK OFFICE
CERTIFICATE OF CORRECTION

| | |
|---|---|
| PATENT NO. | : 6,855,481 B2 |
| APPLICATION NO. | : 10/220364 |
| DATED | : February 15, 2005 |
| INVENTOR(S) | : Kim |

It is certified that error appears in the above-identified patent and that said Letters Patent is hereby corrected as shown below:

11. The apparatus of claim 9, wherein said irradiated material is a semiconductor substrate.

12. The apparatus of claim 9, wherein said irradiated material mover is a wafer mover comprising a wafer cassette installed a plurality of wafers and inserts said wafer between said plurality of lenses.

13. The apparatus of claim 9, wherein said semiconductor substrate has been applied with electron beam resist film after deposition of gate oxide and amorphous silicon on the substrate in which source and drain regions are already formed.

14. A method for forming a pattern using a crystal structure of a single or a poly crystalline material as a mask, comprising the steps of: locating said material having a crystal structure in the chamber of the modified TEM(transmission electron microscopy); radiating an electron beam to said material in said modified TEM(transmission electron microscopy); forming a pattern from a lattice image of said material formed as a result of interference between diffracted electron beams and transmitted electron beams passed through said material; and scaling up or scaling down said pattern on the surface of an irradiated material.

15. The method of claim 14, wherein said lattice image of material is formed by a method of the phase contrast imaging.

16. The method of claim 14, wherein said irradiated material is an electron beam resist material.

17. A method for forming a quantum dot using a crystal structure of a single or a poly crystalline material as a mask, comprising the steps of: locating said material having a crystal structure in the chamber of the modified TEM (transmission electron microscopy); radiating an electron beam to said material in said modified transmission electron microscopy; forming a pattern from a lattice image of said material formed as a result of interference between diffracted electron beams and transmitted electron beams passed through said material; scaling up or scaling down said pattern on the surface of an electron beam resist on a substrate, patterning said electron beam resist.

18. The method of claim 17, wherein said lattice image of material is formed by a method of the phase contrast imaging.

UNITED STATES PATENT AND TRADEMARK OFFICE
CERTIFICATE OF CORRECTION

PATENT NO. : 6,855,481 B2
APPLICATION NO. : 10/220364
DATED : February 15, 2005
INVENTOR(S) : Kim It is certified that error appears in the above-identified patent and that said Letters Patent is hereby corrected as shown below:

19. A semiconductor device, comprising: a semiconductor substrate; a source region located in said semiconductor substrate; a drain region spaced from said source region and located in said semiconductor substrate; a quantum dot layer on a semiconductor substrate region which is located between said source and
drain region and formed by patterning a gate layer using a single or a ploy crystalline material as a mask, said patterning is comprising the steps of: locating said material having a crystal structure in the chamber of the modified TEM(transmission electron microscopy); radiating an electron beam to said material in said modified transmission electron microscopy; forming a pattern from a lattice image of said material formed as a result of interference between diffracted electron beams and transmitted electron beams passed through said material; scaling up or scaling down said pattern on the surface of an electron beam resist on said gate layer, patterning said electron beam resist.

20. The semiconductor device of claim 19, wherein said lattice image of material is formed by a method of the phase contrast imaging.

This certificate supersedes the Certificate of Correction issued December 30, 2008.

Signed and Sealed this

Tenth Day of February, 2009

JOHN DOLL
*Acting Director of the United States Patent and Trademark Office*